United States Patent
Winter et al.

(10) Patent No.: US 9,714,464 B2
(45) Date of Patent: Jul. 25, 2017

(54) PRECURSORS FOR ATOMIC LAYER DEPOSITION

(71) Applicant: WAYNE STATE UNIVERSITY, Detroit, MI (US)

(72) Inventors: Charles H. Winter, Bloomfield Hills, MI (US); Lakmal C. Kalutarage, Detroit, MI (US)

(73) Assignee: Wayne State University, Detroit, MI (US)

( * ) Notice: Subject to any disclaimer, the term of this patent is extended or adjusted under 35 U.S.C. 154(b) by 79 days.

(21) Appl. No.: 14/407,238

(22) PCT Filed: Jun. 11, 2013

(86) PCT No.: PCT/US2013/045144
§ 371 (c)(1),
(2) Date: Dec. 11, 2014

(87) PCT Pub. No.: WO2013/188377
PCT Pub. Date: Dec. 19, 2013

(65) Prior Publication Data
US 2015/0159273 A1 Jun. 11, 2015

Related U.S. Application Data

(60) Provisional application No. 61/658,064, filed on Jun. 11, 2012.

(51) Int. Cl.
*C23C 16/18* (2006.01)
*C23C 16/455* (2006.01)
(Continued)

(52) U.S. Cl.
CPC ........ *C23C 16/45553* (2013.01); *C01B 13/14* (2013.01); *C01B 21/06* (2013.01);
(Continued)

(58) Field of Classification Search
CPC ......... C23C 16/18; C23C 16/34; C23C 16/40; C07C 251/00–251/30
See application file for complete search history.

(56) References Cited

U.S. PATENT DOCUMENTS

2002/0013487 A1    1/2002  Norman et al.
2008/0044687 A1*   2/2008  Bradley ............... C07D 207/20
                                                            428/704

(Continued)

FOREIGN PATENT DOCUMENTS

WO    WO 2010/132871    * 11/2010

OTHER PUBLICATIONS

Evans, D.P., "The Determination of the Paramagnetic Susceptibility of Substances in Solution by Nuclear Magnetic Resonance," J. Chem. Soc. 1959, pp. 2003-2005.

(Continued)

*Primary Examiner* — Elizabeth Burkhart
(74) *Attorney, Agent, or Firm* — Brooks Kushman P.C.

(57) ABSTRACT

Atomic layer deposition (ALD) and chemical vapor deposition (CVD) precursors that are useful for forming metal-containing films are provided. These compounds include triazapentadienyl, α-imino enolate compounds and α-imino ketone compounds having formulae 1, 2, and 3, respectively. An ALD method using the precursors is also provided.

26 Claims, 8 Drawing Sheets

(51) Int. Cl.
  *C07F 13/00*   (2006.01)
  *C07F 15/02*   (2006.01)
  *C01B 13/14*   (2006.01)
  *C01B 21/06*   (2006.01)
  *C07C 251/12*  (2006.01)
  *C07C 251/76*  (2006.01)
  *C22B 15/00*   (2006.01)
  *C22B 23/00*   (2006.01)

(52) U.S. Cl.
  CPC .......... *C07C 251/12* (2013.01); *C07C 251/76* (2013.01); *C07F 13/00* (2013.01); *C07F 15/025* (2013.01); *C22B 15/00* (2013.01); *C22B 23/00* (2013.01); *C23C 16/18* (2013.01)

(56) References Cited

U.S. PATENT DOCUMENTS

| | | | |
|---|---|---|---|
| 2008/0102205 A1 | 5/2008 | Barry et al. | |
| 2010/0130779 A1* | 5/2010 | Norman | C07C 279/12 564/1 |
| 2012/0321817 A1* | 12/2012 | Dussarrat | C23C 16/18 427/569 |
| 2013/0011579 A1* | 1/2013 | Norman | C07F 17/00 427/569 |

OTHER PUBLICATIONS

Kwiatkowski, P. et al., "Catalytic assymetric allylation of aldehydes using the chiral (salen)chromium(III) complexes," Tetrahedron 62 (2006), pp. 5116-5125.

McNAB, H. An Analysis of the 1H and 13C Nuclear Magnetic Resonance Spectra of 3-5-Butylaminoacrolein and of Glyoxal t-Butylhydrazone.

Li, Z. et al, "Atomic Layer Deposition of Ultrathin Copper Metal Films from a Liquid Copper(I) Amidinate Precursor," J. of the Electrochemical Soc., 2006, v. 153(11), pp. C787-C794.

Zhou, M. et al., "Synthesis and Structures of Selected Triazapentadienate of Li, Mn, Fe, Co, Ni, Cu(I), and Cu(II) using 2,4-N,N'-Disubstituted 1,3,5-Triazapentadienate Anions as Ancillary Ligands: [N(Ar)C(NMe2)NC(NMe2)-N(R)]-A (Ar=Ph, 2, 6-iPr2-C6H3; R=H, SiMe3)," Inorganic Chemistry, 2008, v. 47, pp. 6692-6700.

International Search Report dated Sep. 5, 2013 issued in PCT/US2013/045144 (filed Jun. 11, 2013), 3 pgs.

Reedijk, J. et al., "Complexes with Ligands Containing Nitrile Groups. Part VI. Some methyl cyanide adducts of metal chlorides," RECUEIL, 87 (1968), pp. 552-558.

Severin, T. et al., "Reactions with Monohydrazones of Dicarbonyl Compound, IV—New Syntheses of Pyrroles and Pyrrolines," Chem. Ber. 110, pp. 491-499 (1977) and English Abstract.

\* cited by examiner formic acid alkyl carboxylic acid oxalic acid dicarboxylic acids sulfonic acids

HX

Inorganic Acid phosphoric acid phosphorous acid $R^{14}$ = H, $C_1$-$C_8$alkyl, $C_6$-$C_{12}$aryl, $C_1$-$C_8$fluoroalkyl
X = $N_3^-$, $NO_3^-$, halide(e.g., Cl, F, Br)
n = an integer from 1 to 6.

PRECURSORS FOR ATOMIC LAYER DEPOSITION

CROSS-REFERENCE TO RELATED APPLICATIONS

This application is the U.S. National Phase of PCT Appln. No. PCT/US2013/045144 filed Jun. 11, 2013, which claims the benefit of U.S. provisional application Ser. No. 61/658,064 filed Jun. 11, 2012, the disclosures of which are incorporated in their entirety by reference herein.

STATEMENT REGARDING FEDERALLY SPONSORED RESEARCH OR DEVELOPMENT

The invention was made with Government support under Contract No. CHE0910475 awarded by the National Science Foundation. The Government has certain rights in the invention.

FIELD OF THE INVENTION

In at least one aspect, the present invention is related to the formation of metal films from "metalorganic" precursors.

BACKGROUND OF THE INVENTION

The growth of thin films is a central step in the fabrication of many functional materials. In recent years, atomic layer deposition (ALD) has been recognized as an important process for forming thin films for the electronics industry. Synthesizing suitable precursors for ALD growth of transition metal-containing thin films is an important and challenging aspect of this process. Transition metal complexes should possess the following features in order to serve as good precursors in ALD of transition metal-containing thin films: (1) the highest possible volatility to allow the lowest deposition temperatures, (2) high thermal stability throughout the range of desired deposition temperatures, (3) the ability to chemisorb or react with surface sites, and (4) high reactivity with the second precursor (co-reactant that reduces the metal precursor to its metal).

Accordingly, there is a need for the design of novel ALD precursors having the requisite chemical properties.

SUMMARY OF THE INVENTION

The present invention solves one or more problems of the prior art by providing a triazapentadienyl compound that is useful for forming a metal-containing film. The triazapentadienyl compound is described generally by formula (I):

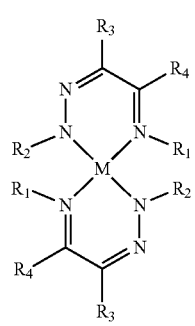

wherein:
M is a metal selected from groups 2 to 12 of the Periodic Table (e.g., Mg, Zn, Cr, Mn, Fe, Co, or Ni);
$R_1$ is $C_{1-8}$ alkyl, $C_{5-12}$ aryl, or $NR_5R_6$;
$R_2$ is $C_{1-8}$ alkyl;
$R_3$, $R_4$ are each independently hydrogen or $C_{1-8}$ alkyl; and
$R_5$, $R_6$ are each independently $C_{1-8}$ alkyl with the proviso that when M is Zn, Mg, Cr, $R_5$ is $C_{2-8}$ alkyl.

In another embodiment, an α-imino enolate compound that is useful for forming a metal-containing film is provided. The α-imino enolate compound is described generally by formula (I):

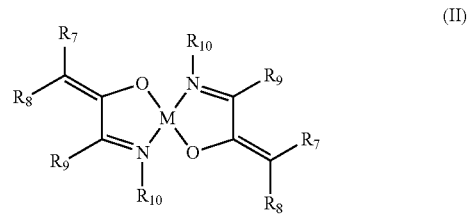

wherein:
M is a metal selected from groups 2 to 12 of the Periodic Table (e.g., Zn, Mg, Cr, Mn, Fe, Co, Ni, or Cu);
$R_7$, $R_8$, $R_9$ are each independently hydrogen, $C_{1-8}$ alkyl, $C_{5-12}$ aryl, or $C_{5-12}$ heteroaryl; and $R_{10}$ is $C_{1-8}$ alkyl, $C_{5-12}$ aryl, or $C_{5-12}$ heteroaryl.

In another embodiment, an α-imino ketonate compound that is useful for forming a metal-containing film is provided. The α-imino ketonate compound is described generally by formula (III):

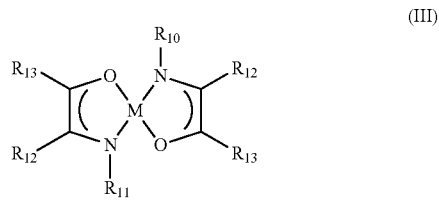

M is a metal selected from groups 2 to 12 of the Periodic Table (e.g., Zn, Mg, Cr, Mn, Fe, Co, Ni, or Cu);
$R_{11}$ is $C_{1-8}$ alkyl, $C_{5-12}$ aryl, or $C_{5-12}$ heteroaryl; and
$R_{12}$, $R_{13}$ are each independently hydrogen, $C_{1-8}$ alkyl, $C_{5-12}$ aryl, or $C_{5-12}$ heteroaryl.

In another embodiment, a method of forming a metal-containing product is provided. The method includes a step of reacting a first compound having bidentate ligands with an reactive compound to form a first product. The first compound is selected from the group consisting of compounds having formula 1, 2 and 3 set forth above.

BRIEF DESCRIPTION OF THE DRAWINGS

Exemplary embodiments of the present invention will become more fully understood from the detailed description and the accompanying drawings, wherein.

DESCRIPTION OF THE INVENTION

Figure 1:
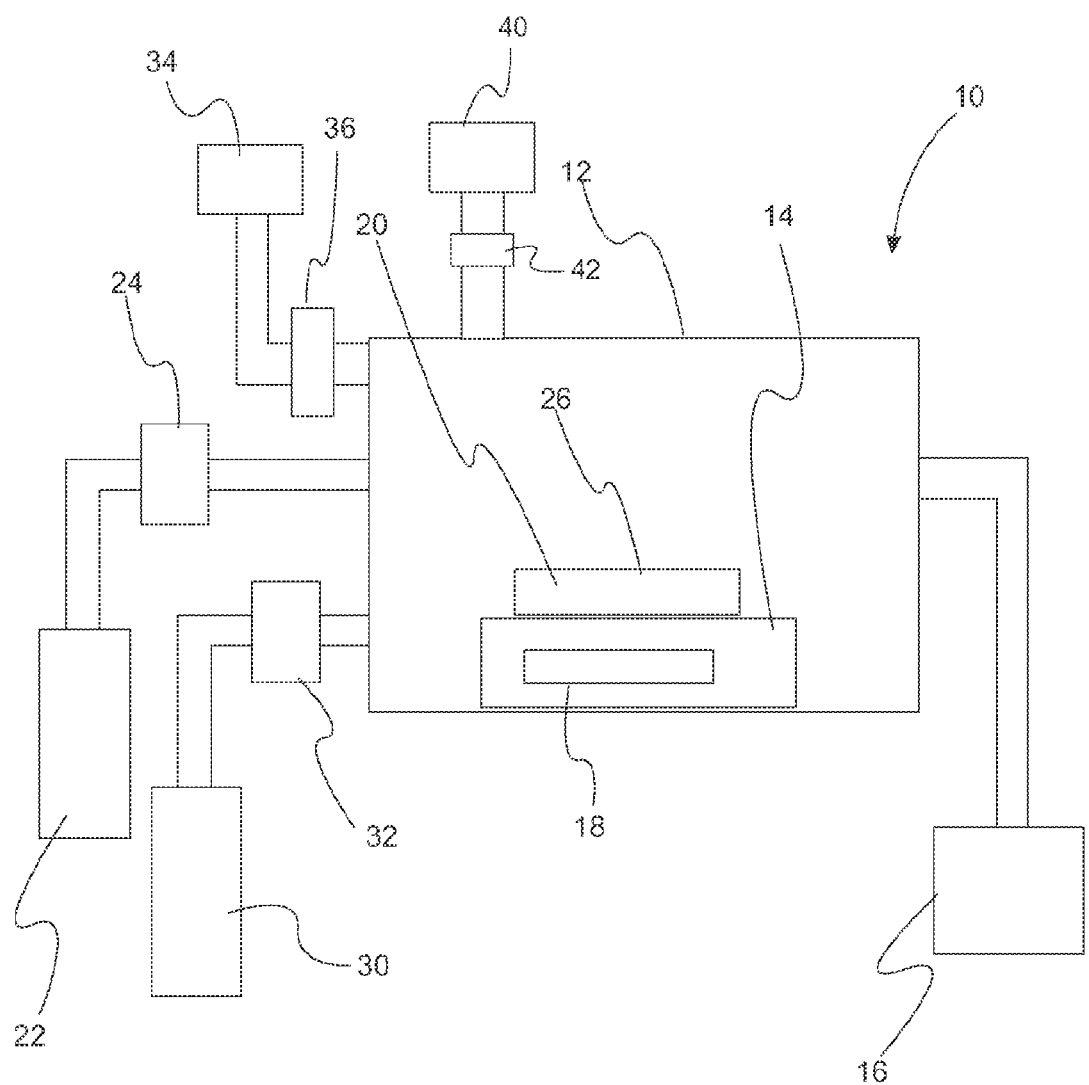
FIG. 1 is a schematic illustration of an ALD deposition system used in an embodiment of the present invention.

Reference will now be made in detail to presently preferred compositions, embodiments and methods of the present invention which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary:percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

In an embodiment, a triazapentadienyl compound that is useful for forming a metal-containing film is provided. The triazapentadienyl compound is described generally by formula (1):

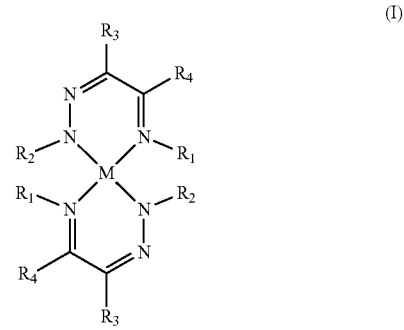

(I)

wherein:

M is a metal selected from groups 2 to 12 of the Periodic Table. In particular, M is Zn, Mg, Cr, Mn, Fe, Co, Ni, or Cu;

$R_1$ is $C_{1-8}$ alkyl, $C_{5-12}$ aryl, or $NR_5R_6$;

$R_2$ is $C_{1-8}$ alkyl;

$R_3$, $R_4$ are each independently hydrogen or $C_{1-8}$ alkyl; and $R_5$, $R_6$ are each independently $C_{1-8}$ alkyl with the proviso that when M is Cr, $R_5$ is $C_{2-8}$ alkyl. In a refinement, when $R_1$ is $C_{1-8}$ alkyl, M is Zn, Mg, Cr, Mn, Fe, Co, or Ni, and when $R_1$ is N $R_5R_6$; M is Zn, Mg, Mn, Fe, Co, or Ni. In a refinement, $R_1$, $R_2$, $R_3$, $R_4$ are each independently methyl, ethyl, n-propyl, isopropyl, n-butyl, sec-butyl, isobutyl, t-butyl, or phenyl. In a particularly useful refinement, $R_2$ is t-butyl.

In a variation of the compound having formula (1), when $R_1$ is $C_{1-8}$ alkyl, M is Cr, Mn, Fe, Co, or Ni, and when $R_1$ is N $R_5R_6$, M is Zn, Mg, Mn, Fe, Co, or Ni. In another variation, $R_1$ is $C_{1-8}$ alkyl and M is Zn, Mg, Cr, Mn, Fe, Co, or Ni. In still another variation, $R_1$ is N $R_5R_6$ and M is Zn, Mg, Mn, Fe, Co, or Ni.

In another embodiment, an α-imino ketonate compound that is useful for the deposition of metal-containing films and, in particular, metal films is provided. The compound of this embodiment is described by formula II:

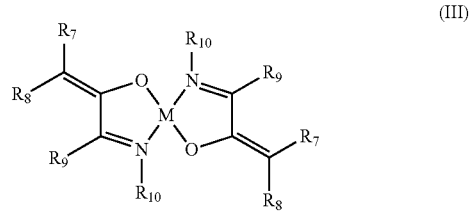

(III)

wherein:

M is a metal selected from groups 2 to 12 of the Periodic Table. In particular, M is Zn, Mg, Cr, Mn, Fe, Co, Ni, or Cu;

$R_7$, $R_8$, $R_9$ are each independently hydrogen, $C_{1-8}$ alkyl, $C_{5-12}$ aryl, or $C_{5-12}$ heteroaryl; and $R_{10}$ is $C_{1-8}$ alkyl, $C_{5-12}$ aryl, or $C_{5-12}$ heteroaryl.

In a refinement, $R_7$, $R_8$, $R_9$, $R_{10}$ are each independently methyl, ethyl, n-propyl, isopropyl, n-butyl, sec-butyl, isobutyl, t-butyl, or phenyl. In a particularly useful refinement, $R_{10}$ is t-butyl. The α-imino enolate complexes of the present embodiment sublime in the range of 100-160° C. at 0.05 Torr and decompose in the temperature range of 190-295° C. making these compounds useful for atomic layer deposition (ALD).

In still another embodiment, an α-imino ketonate compound that is useful for forming a metal-containing film and, in particular, a metal film is provided. The α-imino ketonate compound is described generally by formula (III):

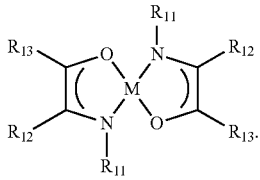

(III)

M is a metal selected from groups 2 to 12 of the Periodic Table. In particular, M is Zn, Mg, Cr, Mn, Fe, Co, Ni, or Cu; $R_{11}$ is $C_{1-8}$ alkyl, $C_{5-12}$ aryl, or $C_{5-12}$ heteroaryl; and $R_{12}$, $R_{13}$ are each independently hydrogen, $C_{1-8}$ alkyl, $C_{5-12}$ aryl, or $C_{5-12}$ heteroaryl.

In a refinement, $R_{11}$, $R_{12}$, $R_{13}$ are each independently methyl, ethyl, n-propyl, isopropyl, n-butyl, sec-butyl, isobutyl, t-butyl, or phenyl. In a particularly useful refinement, $R_{11}$ is t-butyl. The α-imino ketonate complexes of the present embodiment sublime at 100-135° C. at 0.05 Torr and decompose between 180-250° C. making these compounds useful precursors for ALD.

In another embodiment, a method for forming a metal-containing compound includes a step of reacting a compound having bidentate ligands with an reactive compound to form a first product, the first compound selected from the group consisting of:

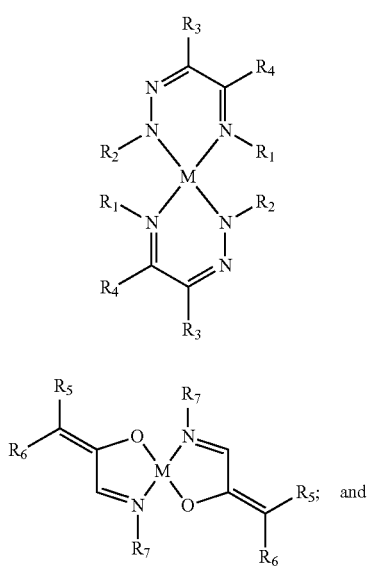

(I)

(II)

-continued

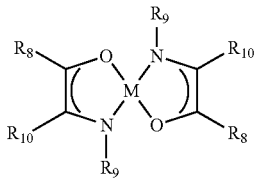

(III)

wherein:
M is a metal selected from groups 2 to 12 of the Periodic Table. In particular, M is Zn, Mg, Cr, Mn, Fe, Co, Ni, or Cu;
$R_1$ is $C_{1-8}$ alkyl, $C_{5-12}$ aryl, or N $R_5R_6$;
$R_2$, $R_3$, $R_4$ are each independently $C_{1-8}$ alkyl;
$R_5$, R6 is $C_{1-8}$ alkyl with the proviso that when M is Cr, $R_5$ is $C_{2-8}$ alkyl; and
$R_5$, $R_6$, $R_7$, $R_8$, $R_9$, $R_{10}$ are each independently $C_{1-8}$ alkyl, $C_{5-12}$ aryl, or $C_{5-12}$ heteroaryl. In a refinement, the reactive compound is a reducing agent. In this variation, the resulting product is a metal (i.e, zero oxidation state). Examples of useful reducing agents include, but are not limited to, molecular hydrogen, atomic hydrogen, silane, disilane, organosilanes, compounds containing Si—H bonds, germane, organogermanes, compounds containing Ge—H bonds, stannane, compounds containing Sn—H bonds, other metal hydride compounds, formic acid, glyoxalic acid, oxalic acid, other carboxylic acids, diborane, compounds containing B—H bonds, hydrazine, carbon-substituted hydrazines, formalin, formaldehyde, organic alcohols, organoaluminum compounds, organozinc compounds, other organometallic compounds, plasma-activated versions of the above compounds. In another refinement, the reactive compound is an oxidizing agent with the resulting product being a metal oxide. Examples of useful oxidizing agents include, but are not limited to, water, ozone, molecular oxygen, atomic oxygen, organic alcohols, hydrogen peroxide, organic hydroperoxides, organic peroxides, nitrous oxide, plasma-activated versions of the above compounds. In still another variation, the activating compound is a nitriding agent (i.e., a nitrogen-containing agent) with the resulting product being a metal nitride. Examples of such nitriding agents include, but are not limited to, ammonia, hydrazine, alkyl-substituted hydrazines, and plasma activated versions thereof.

In another variation, a method for forming a metal-containing film using compounds 1, 2, or 3 is provided. FIG. 1 provides a schematic of an atomic layer deposition system that is useful for forming such films. Deposition system 10 includes reaction chamber 12, substrate holder 14, and vacuum pump 16. Typically, substrate 20 is heated via heater 18. The method has a deposition cycle comprising contacting substrate 20 with a vapor of a metal-containing compound described by formula 1, 2, or 3 as set forth above. In particular, the vapor is introduced from precursor source 22 into reaction chamber 12 for a predetermined pulse time. The pulse time is controlled via control valve 24. At least a portion of the vapor of the metal-containing compound having formula 1, 2, or 3 modifies (e.g, adsorbs or reacts with) substrate surface 26 to form a modified surface. The method further comprises contacting the modified surface with a vapor of a reactive compound from compound source 30 for a predetermined pulse time. The pulse time is controlled via control valve 32. The reactive compound causes the metal-containing compound to react and form at least a portion of the thin metal containing film on the surface of the substrate. The reduced pressure of chamber 12 is maintained by vacuum pump 16.

In a variation of the present embodiment, the method further comprises removing at least a portion of the vapor of the metal containing compound having formula 1, 2, or 3 that is lingering in the gas phase (i.e., has not adsorbed or reacted with the substrate) from the vicinity of the substrate before introducing the vapor of the reactive compound and removing at least a portion of the vapor of the reactive compound from the vicinity of the substrate. The metal-containing compound and reactive compound are removed in purging steps by introducing a purge gas from purge source 34 into reaction chamber 12 for a predetermined purge time. The purge time is controlled by control valve 36.

In another variation, the method further includes at least one additional deposition cycle comprising sequentially contacting the substrate with the vapor of a metal-containing compound having formula 1, 2, or 3 and then the vapor of the reactive compound. In some refinements, the substrate is contacted for a plurality of additional deposition cycles. For example, the substrate may be contacted with from 1 to several thousand deposition cycles depending on the thickness of the film desired.

Figure 2:
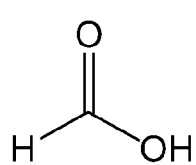
FIG. 2 provides examples of acids that can be reacted with the compounds of having formula 1, 2, and 3.
Figure 2:
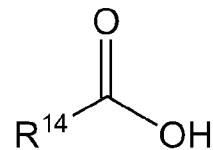
Figure 2:
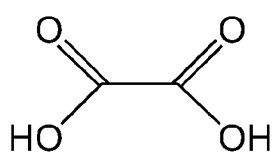
Figure 2:
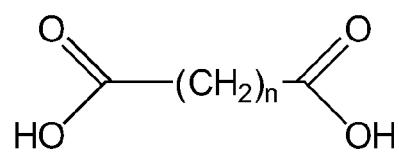
Figure 2:
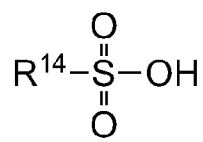
Figure 2:
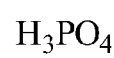
Figure 2:

In another variation, a method for forming a metal-containing film using compounds 1, 2, or 3 is provided. Referring again to FIG. 1, deposition system 10 includes reaction chamber 12, substrate holder 14, and vacuum pump 16. Typically, the substrate is heated via heater 18. The method has a deposition cycle comprising contacting substrate 20 with a vapor of a metal-containing compound described by formula 1, 2, or 3 as set forth above. In particular, the vapor is introduced from precursor source 22 into reaction chamber 12 for a predetermined pulse time. The pulse time is controlled via control valve 24. At least a portion of the vapor of the metal-containing compound having formula 1, 2, or 3 modifies (e.g, adsorbs or reacts with) substrate surface 26 to form a modified surface. In the next reaction step of the deposition cycle, an acid such as formic acid is then introduced from acid source 40 into reaction chamber 12 for a second predetermined pulse time. The second predetermined pulse time is controlled by valve 42. Examples of other suitable acids are provided in FIG. 2. In FIG. 2, $R^{14}$ is H (i.e., hydride), $C_{1-8}$ alkyl, $C_{6-12}$ aryl, or $C_{1-8}$ fluoroalkyl, X is $N_3^-$, $NO_3$, halide (e.g., Cl, F, Br), and n is an integer from 1 to 6. In a refinement, $R^{14}$ is hydride, $C_{1-4}$ alkyl, $C_{6-10}$ aryl, or $C_{1-4}$ fluoroalkyl, X is $N_3^-$, $NO_3^-$, halide (e.g., Cl, F, Br), and n is an integer from 1 to 6. Examples of useful alkyl groups include, but are not limited to, methyl, ethyl, n-propyl, isopropyl, n-butyl, t-butyl, isobutyl, sec-butyl, and the like. Examples of useful aryl groups include, but are not limited to, phenyl, tolyl, naphthyl, and the like. It should also be appreciated that R, $R^1$, $R^2$ may be optionally substituted with groups such as halide. The second predetermined pulse time should be sufficiently long that available binding sites on the first modified substrate surface are saturated and a second modified surface is formed. Typically, the second predetermined pulse time is from 0.1 second to 20 seconds. The second predetermined pulse time is controlled via control valve 32. Reaction chamber 12 is then purged with an inert gas for a second purge time (typically, 0.5 seconds to 2 minutes as set forth above).

In the final reaction step of the deposition cycle, a reducing agent is then introduced from reductant source 30 into reaction chamber 12 for a third predetermined time. Examples of suitable reducing agents include, but are not limited to, hydrazine, hydrazine hydrate, alkyl hydrazines, 1,1-dialkylhydrazines, 1,2-dialkylhydrazines, $H_2$, $H_2$ plasma, ammonia, ammonia plasma, silanes, disilanes, trisilanes, germanes, diborane, formalin, amine borane, dialkyl zinc, alkyl aluminum, alkyl gallium, alkyl indium complexes, and other plasma-based gases, and combinations thereof. The third predetermined pulse time should be sufficiently long that available binding sites on the second modified substrate surface are saturated with a metal layer being formed thereon. Typically, the third predetermined pulse time is from 0.1 second to 20 seconds. Reaction chamber 12 is then purged with an inert gas for a third purge time (typically, 0.5 seconds to 2 minutes as set forth above).

In a variation as set forth above, the method further comprises removing at least a portion of the vapor of the metal containing compound having formula 1, 2, or 3 that is lingering in the gas phase (i.e., has not adsorbed or reacted with the substrate) from the vicinity of the substrate before introducing the vapor of the reactive compound and removing at least a portion of the vapor of the reactive compound from the vicinity of the substrate. The metal-containing compound and reactive compound are removed in purging steps by introducing a purge gas from purge source 34 into reaction chamber 12 for a predetermined purge time. The purge time is controlled by control valve 36.

Pulse times and purge times also depend on the properties of the chemical precursors and the geometric shape of the substrates. Thin film growth on flat substrates uses short pulse and purge times, but pulse and purge times in ALD growth on 3-dimensional substrates can be very long. Therefore, in one refinement, pulse times and purge times are each independently from about 0.0001 to 200 seconds. In another refinement, pulse and purge times are each independently from about 0.1 to about 10 seconds.

In the film forming methods set forth above, the specific type of reactive compound that will be used depends on the particular metal compound to be made. If a metal film is to be made, the reactive compound will be a reducing agent as set forth above. If a metal oxide film is made, the reactive compound is an oxidizing agent as set forth above. If a nitride film is made, the reactive compound is a nitriding agent as set forth above.

During film formation by the methods, the substrate temperature will be at a temperature suitable to the properties of the chemical precursor(s) and film to be formed. In a refinement of the method, the substrate is set to a temperature from about 0 to 1000° C. In another refinement of the method, the substrate has a temperature from about 50 to 450° C. In another refinement of the method, the substrate has a temperature from about 100 to 250° C. In still another refinement of the method, the substrate has a temperature from about 150 to 400° C. In another refinement of the method, the substrate has a temperature from about 200 to 300° C.

The desired metal film thickness depends on the number of deposition cycles. Therefore, in a refinement, the deposition cycle is repeated a plurality of times to form a predetermined thickness of the metal film. In a further refinement, the deposition cycle is repeated a plurality of times to form a metal film having a thickness from about 5 nanometers to about 200 nanometers. In still another refinement, the deposition cycle is repeated a plurality of times to form a metal film having a thickness from about 5 nanometers to about 300 nanometers. In yet another refinement, the deposition cycle is repeated a plurality of times to form a metal film having a thickness from about 5 nanometers to about 100 nanometers.

During film formation by the method of the present embodiment, the substrate temperature will be at a temperature suitable to the properties of the chemical precursor(s) and film to be formed. In a refinement of the method, the substrate is set to a temperature from about 0 to 1000° C. In another refinement of the method, the substrate has a temperature from about 50 to 450° C. In another refinement of the method, the substrate has a temperature from about 100 to 250° C. In still another refinement of the method, the substrate has a temperature from about 150 to 400° C. In another refinement of the method, the substrate has a temperature from about 200 to 300° C.

Similarly, the pressure during film formation is set at a value suitable to the properties of the chemical precursors and film to be formed. In one refinement, the pressure is from about $10^{-6}$ Torr to about 760 Torr. In another refinement, the pressure is from about 0.1 millitorr to about 10 Torr. In still another refinement, the pressure is from about 1 to about 100 millitorr. In yet another refinement, the pressure is from about 1 to 20 millitorr.

The following examples illustrate the various embodiments of the present invention. Those skilled in the art will recognize many variations that are within the spirit of the present invention and scope of the claims.

Experimental Section 1

General Considerations.

All manipulations were carried out under argon using either Schlenk or glove box techniques, except that the ligands were prepared in ambient atmosphere. Tetrahydrofuran was distilled from sodium benzophenone ketyl, and hexane was distilled from $P_2O_5$. Anhydrous transition metal chlorides ($CrCl_2$, $MnCl_2$, $FeCl_2$, $CoCl_2$, and $NiCl_2$) were obtained from Strem Chemicals Inc. and used as received. $NiCl_2 \cdot CH_3CN$ was prepared according to a literature procedure.[1] Potassium hydride (30 wt % dispersion in mineral oil; washed with hexane before use), tert-butyl amine, and 1,1-dimethylhydrazine were purchased from Sigma-Aldrich. tert-Butyl hydrazine hydrochloride was purchased from Acros Organics. Glyoxal was purchased from Alfa Aesar.

$^1H$ and $^{13}C\{^1H\}$ NMR spectra were obtained at 400 and 100 MHz in benzene-$d_6$ or chloroform-d and were referenced to the residual proton and the $^{13}C$ resonances of the solvents. Infrared spectra were obtained using Nujol as the medium. Melting points were obtained on a Thermo Scientific Mel-Temp 3.0 digital melting point apparatus and are uncorrected. Thermogravimetric analyses (TGA) were carried out with a SDT-2960 TGA/DTA instrument. Magnetic moments were determined in the solid state using a Johnson Mathey magnetic susceptibility apparatus, and by $^1H$ NMR in benzene solution using the Evans method.

Preparation of 1,5-di-test-butyl-1,2,5-triazapentadiene 2-(2-(tert-butyl)hydrazono)acetaldehyde was prepared according to a published procedure.[3] A 100 mL round bottom flask was charged with a magnetic stir bar, 2-(2-(tert-butyl)hydrazono)acetaldehyde (1.000 g, 7.80 mmol), and diethyl ether (15 mL). To this stirred solution at ambient temperature was slowly added tert-butyl amine (0.83 mL, 7.80 mmol) and the solution was stirred for 4 h. The resultant yellow solution was washed with water (20 mL) and the organic layer was separated. The organic layer was dried over anhydrous $Na_2SO_4$ and the volatile components were removed under reduced pressure. Light yellow crystals were obtained by sublimation of the crude solid at 80° C./0.05 Torr (0.786 g, 55%): mp 200° C.; IR (Nujol, cm$^{-1}$) 3144 (m), 1620 (m), 1547 (m), 1365 (m), 1346 (m), 1304 (w), 1260 (w), 1222 (m) 1166 (m), 1096 (w), 1026 (w), 970 (w), 883 (w), 799 (w); $^1H$ NMR (CDCl$_3$, 23° C., δ) 7.84 (s, 1H, CHN), 7.30 (s, 1H, CHN), 5.28 (s, broad 1H, NH), 1.22 (s, 9H, C(CH$_3$)$_3$), 1.21 (s, 9H, C(CH$_3$)$_3$); $^{13}C\{^1H\}$ NMR (CDCl$_3$, 23° C., ppm) 155.22 (s, CHN), 137.35 (s, CHN), 56.91 (s, C(CH$_3$)$_3$), 54.50 (s, C(CH$_3$)$_3$), 29.65 (s, C(CH$_3$)$_3$), 28.57 (s, C(CH$_3$)$_3$); ESI-HRMS: calcd for $C_{10}H_{22}N_3$ ([M+H]$^+$) 184.1814, found 184.1814.

Preparation of 1-tert-butyl-5-dimethylamino-1,2,5-triazapentadiene 2-(2,2-Dimethylhydrazono)acetaldehyde was prepared according to a published procedure.[4] A 100 mL round bottom flask was charged with a magnetic stir bar, 2-(2,2-dimethylhydrazono)acetaldehyde (1.000 g, 9.98 mmol), and water (20 mL). To this stirred solution at ambient temperature was slowly added a mixture of tert-butyl hydrazine hydrochloride (1.370 g, 11.00 mmol) and potassium hydroxide (0.726 g, 11.00 mmol) in water (30 mL). This solution was stirred for 15 min and was set aside for 18 hours. An oil formed initially, which converted to a yellow solid over this time. The solution was filtered and the solid was dried using a desiccator filled with $P_2O_5$. Light yellow crystals were obtained by sublimation at 60° C./0.05 Torr (1.120 g, 66%): mp 56° C.; IR (Nujol, cm$^{-1}$) 3214 (m), 1559 (w), 1365 (m), 1300 (w), 1261 (w), 1229 (w) 1132 (w), 1038 (m), 1022 (m); $^1H$ NMR (C$_6$D$_6$, 23° C., δ) 7.49 (d, 1H, (J=8.0 Hz), CH), 7.17 (d, 1H, (J=8.0 Hz), CH), 4.65 (s, broad 1H, NH), 2.47 (s, 6H, N(CH$_3$)$_2$), 1.14 (s, 9H, C(CH$_3$)$_3$); $^{13}C\{^1H\}$ NMR (100 MHz, benzene-$d_6$, 23° C., ppm) 139.26 (s, CHN), 133.22 (s, CHN), 53.44 (s, C(CH$_3$)$_3$), 42.26 (s, N(CH$_3$)$_2$), 28.66 (s, C(CH$_3$)$_3$); ESI-HRMS: calcd for $C_8H_{19}N_4$ ([M+H]$^+$) 171.1610, found 171.1607.

Preparation of Bis(1,5-di-test-butyl-1,2,5-triazapentadienyl)nickel(II) (1)

A 100 mL Schlenk flask was charged with a magnetic stir bar, 1,5-di-tert-butyl-1,2,5-triazapentadiene (1.000 g, 5.45 mmol), and tetrahydrofuran (30 mL). To this stirred solution at ambient temperature was slowly added potassium hydride (0.241 g, 6.00 mmol), and the solution was stirred for 4 h. This solution was then slowly added dropwise by cannula to a stirred suspension of anhydrous $NiCl_2 \cdot CH_3CN$ (0.456 g, 2.70 mmol) in tetrahydrofuran (40 mL) at −78° C. The resultant dark brown solution was stirred for 15 h at ambient temperature. The volatile components were then removed under reduced pressure, and the resultant dark red powder was dissolved in hexane (60 mL). The solution was filtered through a 1 cm pad of Celite on a coarse glass frit, and the hexane was then removed under reduced pressure. Dark red crystals of 1 were obtained by sublimation at 155° C./0.05 Torr (0.397 g, 35%): mp 262° C.; IR (Nujol, cm$^{-1}$) 1548 (m), 1365 (s), 1339 (m), 1253 (w), 1213 (m), 1174 (m), 1060 (w), 791 (w); $^1H$ NMR (C$_6$D$_6$, 23° C., δ) 16.64 (s, broad 18H, C(CH$_3$)$_3$), 15.20 (s, broad 18H, C(CH$_3$)$_3$); $\mu_{eff}$=2.84 and 2.86 $\mu_B$ in the solid state and in benzene solution, respectively. Anal. Calcd for $C_{20}H_{40}NiN_6$: C, 56.75; H, 9.53; N, 19.86. Found: C, 56.66; H, 9.49; N, 19.84.

Preparation of Bis(1,5-di-tert-butyl-1,2,5-triazapentadienyl)cobalt(II) (2)

In a fashion similar to the preparation of 1, treatment of anhydrous cobalt(II) chloride (0.350 g, 2.70 mmol) in tetrahydrofuran (40 mL) with a solution of potassium 1,5-di-tert-butyl-1,2,5-triazapentadienate (prepared from 1,5-di-tert-butyl-1,2,5-triazapentadiene (1.000 g, 5.45 mmol) and potassium hydride (0.241 g, 6.00 mmol) in tetrahydrofuran (30 mL)) for 15 h at ambient temperature afforded 2 (0.623 g, 57%) as dark green crystals upon sublimation at 160° C./0.05 Torr: mp 260° C.; IR (Nujol, cm$^{-1}$) 1542 (s), 1364 (s), 1354 (s), 1340 (s), 1255 (m), 1214 (m), 1178 (s), 1054 (m), 996 (w), 790 (m); $\mu_{eff}$=3.78 and 3.95 $\mu_B$ in the solid state and in benzene solution, respectively. Anal. Calcd for $C_{20}H_{40}CoN_6$: C, 56.72; H, 9.52; N, 19.84. Found: C, 56.59; H, 9.46; N, 19.79.

Preparation of Bis(1,5-di-test-butyl-1,2,5-triazapentadienyl)iron(II) (3)

In a fashion similar to the preparation of 1, treatment of anhydrous iron(II) chloride (0.342 g, 2.70 mmol) in tetrahydrofuran (40 mL) with a solution of potassium 1,5-di-tert-butyl-1,2,5-triazapentadienate (prepared from 1,5-di-tert-butyl-1,2,5-triazapentadiene (1.000 g, 5.45 mmol) and potassium hydride (0.241 g, 6.00 mmol) in tetrahydrofuran (30 mL)) for 15 h at ambient temperature afforded 3 (0.805 g, 73%) as dark red crystals upon sublimation at 175° C./0.05 Torr: mp 275° C.; IR (Nujol, cm$^{-1}$) 1529 (s), 1362 (m), 1350 (m), 1336 (s), 1254 (m), 1242 (m), 1215 (m), 1176 (s), 1055 (m), 994 (m), 926 (m), 918 (m), 791 (m); $\mu_{eff}$=5.00 and 4.92 $\mu_B$ in the solid state and in benzene solution, respectively. Anal. Calcd for $C_{20}H_{40}FeN_6$: C, 57.14; H, 9.59; N, 19.99. Found: C, 57.76; H, 9.29; N, 20.14.

Preparation of Bis(1,5-di-test-butyl-1,2,5-triazapentadienyl)manganese(II) (4)

In a fashion similar to the preparation of 1, treatment of anhydrous manganese(II) chloride (0.340 g, 2.70 mmol) in tetrahydrofuran (40 mL) with a solution of potassium 1,5-di-tert-butyl-1,2,5-triazapentadienate (prepared from 1,5-di-tert-butyl-1,2,5-triazapentadiene (1.000 g, 5.45 mmol) and potassium hydride (0.241 g, 6.00 mmol) in tetrahydrofuran (30 mL)) for 15 h at ambient temperature afforded 4 (0.597 g, 54%) as dark yellow crystals upon sublimation at 165° C./0.05 Torr: mp 284° C.; IR (Nujol, cm$^{-1}$) 1552 (m), 1366 (m), 1346 (m), 1257 (m), 1176 (m), 1052 (w), 786 (w); $\mu_{eff}$=5.89 and 5.85 $\mu_B$ in the solid state and in benzene solution, respectively. Anal. Calcd for $C_{20}H_{40}MnN_6$: C, 57.26; H, 9.61; N, 20.03. Found: C, 57.55; H, 9.50; N, 20.12.

Preparation of Bis(1,5-di-test-butyl-1,2,5-triazapentadienyl)chromium(II) (5)

In a fashion similar to the preparation of 1, treatment of anhydrous chromium(II) chloride (0.332 g, 2.70 mmol) in tetrahydrofuran (40 mL) with a solution of potassium 1,5-di-tert-butyl-1,2,5-triazapentadienate (prepared from 1,5-di-tert-butyl-1,2,5-triazapentadiene (1.000 g, 5.45 mmol) and potassium hydride (0.241 g, 6.00 mmol) in tetrahydrofuran (30 mL)) for 15 h at ambient temperature afforded 5 (0.602 g, 55%) as brown crystals upon sublimation at 165° C./0.05 Torr mp 257° C.; IR (Nujol, cm$^{-1}$) 1500 (w), 1366 (m), 1351 (m), 1334 (m), 1313 (w), 1266 (s), 1231 (w), 1211 (w), 1179 (s), 1143 (m), 1135 (m), 1046 (m), 967 (s), 792 (m); $\mu_{eff}$=4.85 and 4.96 $\mu_B$ in the solid state and in benzene solution, respectively. Anal. Calcd for $C_{20}H_{40}CrN_6$: C, 57.67; H, 9.68; N, 20.17. Found: C, 57.98; H, 9.48; N, 20.19.

Preparation of Bis(1,5-di-test-butyl-1,2,5-triazapentadienyl)magnesium(II) (6)

In a fashion similar to the preparation of 1, treatment of anhydrous magnesium(II) bromide (0.497 g, 2.70 mmol) in tetrahydrofuran (40 mL) with a solution of potassium 1,5-di-tert-butyl-1,2,5-triazapentadienate (prepared from 1,5-di-tert-butyl-1,2,5-triazapentadiene (1.000 g, 5.45 mmol) and potassium hydride (0.241 g, 6.00 mmol) in tetrahydrofuran (30 mL)) for 15 h at ambient temperature afforded 6 (0.886 g, 81%) as yellow crystals upon sublimation at 165° C./0.05 Torr: mp 268° C.; IR (Nujol, cm$^{-1}$) 1500 (w), 1366 (m), 1351 (m), 1334 (m), 1313 (w), 1266 (s), 1231 (w), 1211 (w), 1179 (s), 1143 (m), 1135 (m), 1046 (m), 967 (s), 792 (m); $^1$H NMR ($C_6D_6$, 23° C., δ) 6.87 (d, (J=4.4 Hz), 1H, CHN), 6.77 (d, (J=4.4 Hz), 1H, CHN), 1.45 (s, 18H, $C(CH_3)_3$), 1.06 (s, 18H, $C(CH_3)_3$); Anal. Calcd for $C_{20}H_{40}MgN_6$: C, 61.77; H, 10.37; N, 21.61. Found: C, 61.92; H, 10.33; N, 21.76.

Preparation of Bis(1-tert-butyl-5-dimethylamino-1,2,5-triazapentadienyl)nickel(II) (7)

In a fashion similar to the preparation of 1, treatment of anhydrous $NiCl_2 \cdot CH_3CN$ (0.490 g, 2.95 mmol) in tetrahydrofuran (40 mL) with a solution of potassium 1-tert-butyl-5-dimethylamino-1,2,5-triazapentadienate (prepared from 1-tert-butyl-5-dimethylamino-1,2,5-triazapentadiene (1.000 g, 5.90 mmol) and potassium hydride (0.259 g, 6.50 mmol) in tetrahydrofuran (30 mL)) for 15 h at ambient temperature afforded 7 (0.267 g, 23%) as dark red crystals upon sublimation at 105° C./0.05 Torr: mp 99° C.; IR (Nujol, cm$^{-1}$) 1535 (w), 1366 (m), 1351 (m), 1317 (m), 1255 (m), 1195 (m), 1174 (m), 1055 (m), 1037 (m), 961 (m), 792 (m); $^1$H NMR ($C_6D_6$, 23° C., δ) 32.57 (s, broad 12H, $N(CH_3)_2$), 16.53 (s, broad 18H, $C(CH_3)_3$); $\mu_{eff}$=2.86 and 2.85 $\mu_B$ in the solid state and in benzene solution, respectively. Anal. Calcd for $C_{16}H_{34}NiN_8$: C, 48.38; H, 8.63; N, 28.21. Found: C, 48.27; H, 8.53; N, 28.23.

Preparation of Bis(1-tert-butyl-5-dimethylamino-1,2,5-triazapentadienyl)cobalt(II) (8)

In a fashion similar to the preparation of 1, treatment of anhydrous cobalt(II) chloride (0.376 g, 2.95 mmol) in tetrahydrofuran (40 mL) with a solution of potassium 1-tert-butyl-5-dimethylamino-1,2,5-triazapentadienate (prepared from 1-tert-butyl-5-dimethylamino-1,2,5-triazapentadiene (1.000 g, 5.90 mmol) and potassium hydride (0.259 g, 6.50 mmol) in tetrahydrofuran (30 mL)) for 15 h at ambient temperature afforded 8 (0.301 g, 27%) as dark green crystals upon sublimation at 105° C./0.05 Torr: mp 105° C.; IR (Nujol, cm$^{-1}$) 1529 (m), 1366 (m), 1352 (s), 1316 (m), 1256 (m), 1235 (m), 1216 (m), 1198 (m), 1178 (m), 1051 (m), 1029 (m), 963 (m), 789 (m), 779 (m); $\mu_{eff}$=3.92 and 3.95 $\mu_B$ in the solid state and in benzene solution, respectively. Anal. Calcd for $C_{16}H_{34}CoN_8$: C, 48.35; H, 8.62; N, 28.19. Found: C, 48.24; H, 8.66; N, 28.14.

Preparation of Bis(1-tert-butyl-5-dimethylamino-1,2,5-triazapentadienyl)iron(II) (9)

In a fashion similar to the preparation of 1, treatment of anhydrous iron(II) chloride (0.374 g, 2.95 mmol) in tetrahydrofuran (40 mL) with a solution of potassium 1-tert-butyl-5-dimethylamino-1,2,5-triazapentadienate (prepared from 1-tert-butyl-5-dimethylamino-1,2,5-triazapentadiene (1.000 g, 5.90 mmol) and potassium hydride (0.259 g, 6.50 mmol) in tetrahydrofuran (30 mL)) for 15 h at ambient temperature afforded 9 (0.190 g, 18%) as dark green crystals upon sublimation at 105° C./0.05 Torr: mp 106° C.; IR (Nujol, cm$^{-1}$) 1515 (w), 1368 (m), 1351 (m), 1312 (w), 1258 (w), 1196 (w), 1176 (w), 1026 (w), 794 (w); $\mu_{eff}$=4.78 and 4.82 $\mu_B$ in the solid state and in benzene solution, respectively. Anal. Calcd for $C_{16}H_{34}FeN_8$: C, 48.73; H, 8.69; N, 28.42. Found: C, 49.05; H, 8.72; N, 28.10.

Preparation of Bis(1-tert-butyl-5-dimethylamino-1,2,5-triazapentadienyl)manganese(II) (10)

In a fashion similar to the preparation of 1, treatment of anhydrous manganese(II) chloride (0.371 g, 2.95 mmol) in tetrahydrofuran (40 mL) with a solution of potassium 1-tert-butyl-5-dimethylamino-1,2,5-triazapentadienate (prepared from 1-tert-butyl-5-dimethylamino-1,2,5-triazapentadiene (1.000 g, 5.90 mmol) and potassium hydride (0.259 g, 6.50 mmol) in tetrahydrofuran (30 mL)) for 15 h at ambient temperature afforded 10 (0.350 g, 32%) as dark orange crystals upon sublimation at 105° C./0.05 Torr: mp 108° C.; IR (Nujol, cm$^{-1}$) 1539 (m), 1357 (m), 1323 (m), 1256 (m), 1196 (m), 1186 (m), 1152 (w), 1048 (m), 957 (w), 1021 (m), 786 (w), 730 (w); $\mu_{eff}$=5.80 and 5.82 $\mu_B$ in the solid state and in benzene solution, respectively. Anal. Calcd for $C_{16}H_{34}MnN_8$: C, 48.84; H, 8.71; N, 28.48. Found: C, 48.86; H, 8.78; N, 28.32.

Preparation of Bis(1-tert-butyl-5-dimethylamino-1,2,5-triazapentadienyl)magnesium(II) (11)

In a fashion similar to the preparation of 1, treatment of anhydrous magnesium(II) bromide (0.543 g, 2.95 mmol) in tetrahydrofuran (40 mL) with a solution of potassium 1-tert-butyl-5-dimethylamino-1,2,5-triazapentadienate (prepared from 1-tert-butyl-5-dimethylamino-1,2,5-triazapentadiene (1.000 g, 5.90 mmol) and potassium hydride (0.259 g, 6.50 mmol) in tetrahydrofuran (30 mL)) for 15 h at ambient temperature afforded 11 (0.689 g, 63%) as yellow crystals upon sublimation at 165° C./0.05 Torr: mp 113° C.; IR (Nujol, cm$^{-1}$) 1529 (m), 1366 (m), 1352 (s), 1316 (m), 1256 (m), 1235 (m), 1216 (m), 1198 (m), 1178 (m), 1051 (m), 1029 (m), 963 (m), 789 (m), 779 (m); $^1$H NMR ($C_6D_6$, 23° C., δ) 6.73 (d, (J=4.4 Hz), 1H, CHN), 6.71 (d, (J=4.4 Hz), 1H, CHN), 2.31 (s, 18H, $C(CH_3)_3$), 1.45 (s, 18H, $C(CH_3)_3$); Anal. Calcd for $C_{16}H_{34}MgN_8$: C, 52.97; H, 9.45; N, 30.89. Found: C, 52.82; H, 9.66; N, 30.83.

The following reaction scheme shows the synthesis of bis(1,2,5-triazapentadienyl) transition metal complexes.

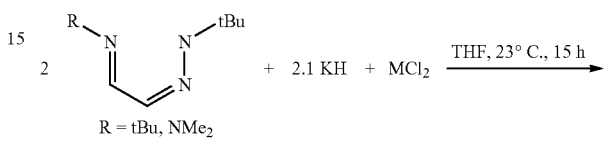

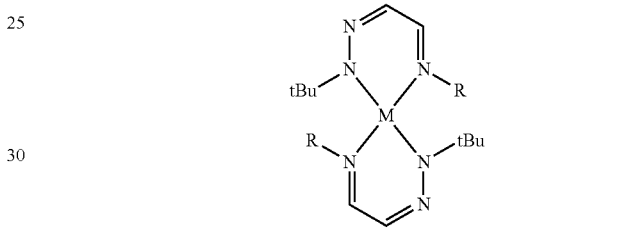

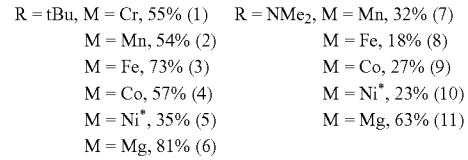

R = tBu, M = Cr, 55% (1)   R = NMe$_2$, M = Mn, 32% (7)
M = Mn, 54% (2)   M = Fe, 18% (8)
M = Fe, 73% (3)   M = Co, 27% (9)
M = Co, 57% (4)   M = Ni*, 23% (10)
M = Ni*, 35% (5)   M = Mg, 63% (11)
M = Mg, 81% (6)

*NiCl$_2$(CH$_3$CN) was used

TABLE 1

| | Thermal properties of the complexes | | | | |
|---|---|---|---|---|---|
| Complex | Sublimation temperature (° C./0.05 Torr) | Melting point (° C.) | Solid state decomposition temperature (° C.) | % Recovery | % Non volatile residue |
| 1 | 175 | 255-257 | 280 | 97 | 3 |
| 2 | 165 | 282-284 | 310 | 97 | 2 |
| 3 | 175 | 273-275 | 310 | 98 | <1 |
| 4 | 160 | 258-260 | 296 | 98 | 1 |
| 5 | 155 | 260-262 | 290 | 98 | 1 |
| 6 | 165 | 268-270 | 290 | 96 | 3 |
| 7 | 105 | 106-108 | 200 | 95 | 4 |
| 8 | 105 | 104-106 | 181 | 93 | 5 |
| 9 | 105 | 103-105 | 225 | 94 | 5 |
| 10 | 105 | 97-99 | 188 | 95 | 4 |
| 11 | 105 | 113-114 | 180 | 95 | 3 |

Figure 3:
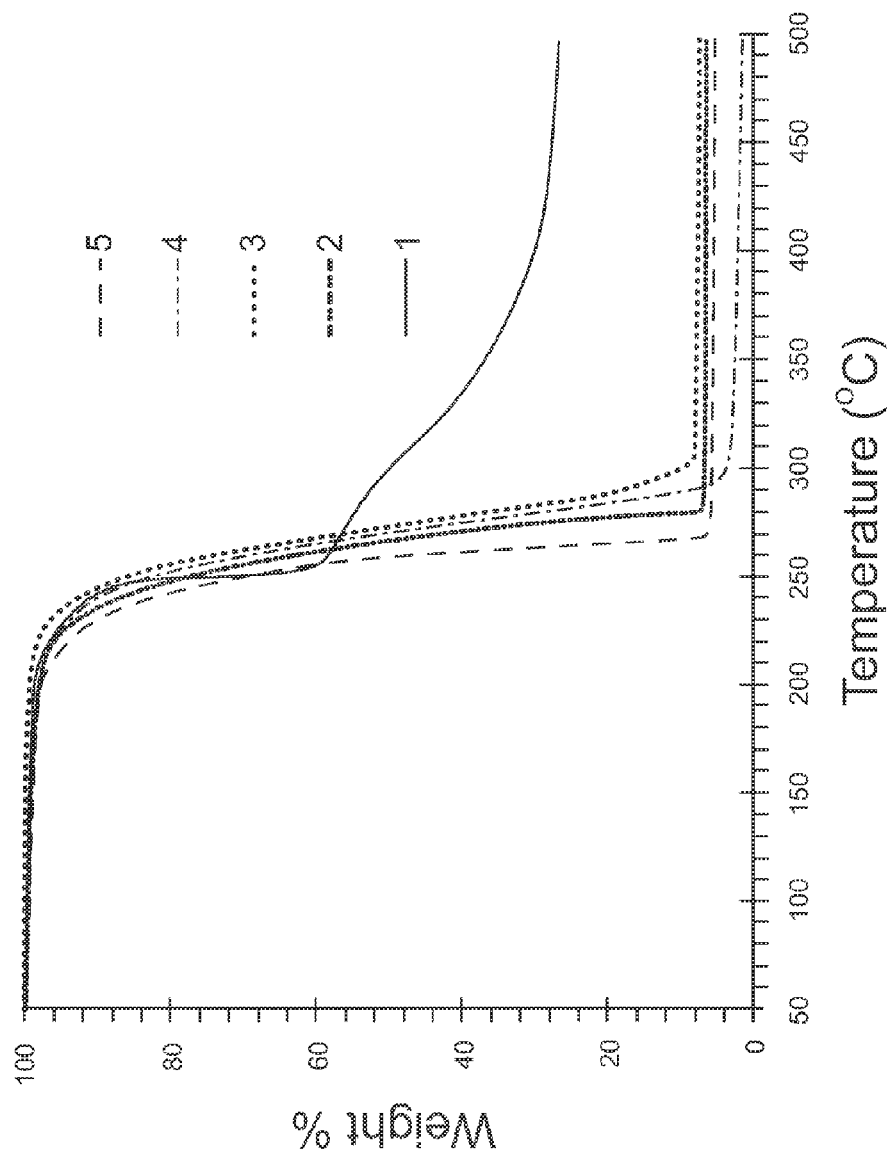
FIG. 3 provides thermogravimetric analysis (TGA) for compounds 1-5.
Figure 4:
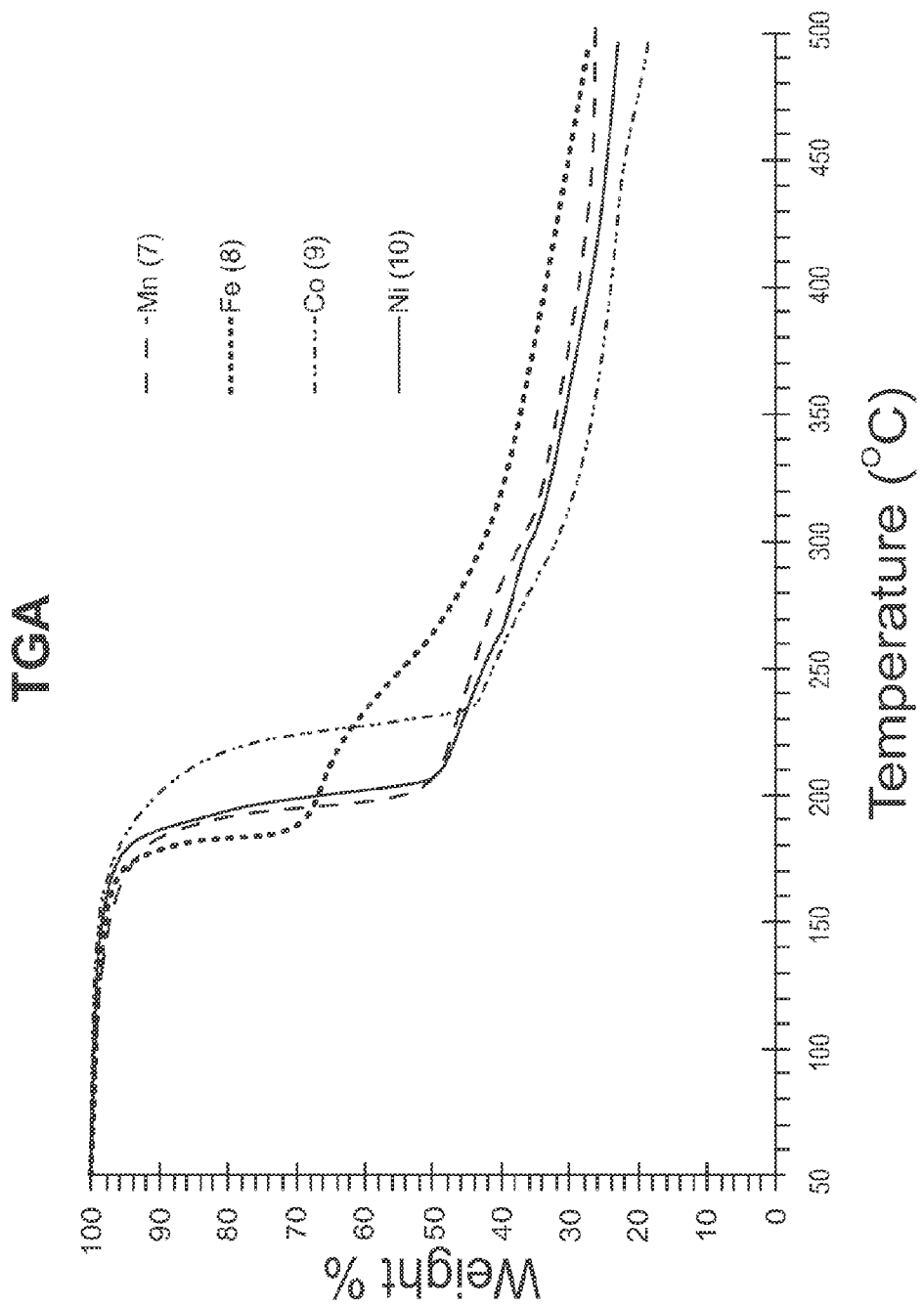
FIG. 4 provides thermogravimetric analysis (TGA) for compounds 7-10.

FIG. 3 provides TGA curves for compounds 1-5 and FIG. 3 provides TGA curves for compounds 7-10.

Solution phase reactivity.

Figure 5:
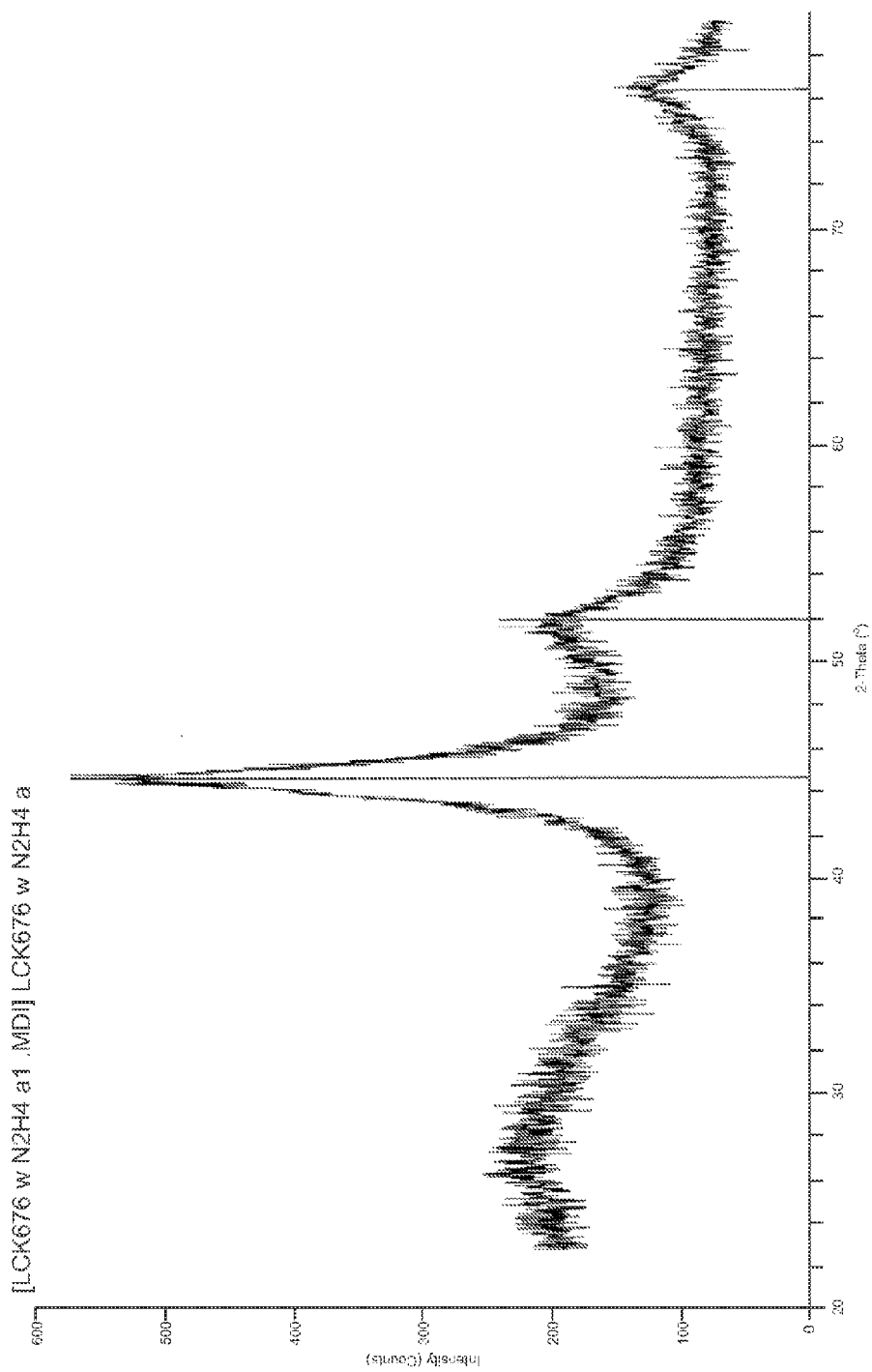
FIG. 5 provides an X-ray Powder Diffraction Spectrum of nickel metal produced upon treatment of compound 10 with hydrazine.

To assess initial viability for use in ALD film growth, 10 (Bis(1-tert-butyl-5-dimethylamino-1,2,5-triazapentadienyl)nickel(II)) was treated with anhydrous hydrazine in tetrahydrofuran at 23° C. A metallic black precipitate was observed within 0.25 h. The precipitate stuck to the magnetic stir bar and a powder X-ray diffraction spectrum indicated the formation of nickel metal (FIG. 5).

Experimental Section 2

General Considerations.

All manipulations were carried out under argon using either Schlenk or glove box techniques, except the ligands were prepared in ambient atmosphere. Tetrahydrofuran was distilled from sodium benzophenone ketyl, hexane was distilled from $P_2O_5$. Anhydrous transition-metal chlorides ($CuCl_2$, $NiCl_2$, $CoCl_2$, $FeCl_2$, $MnCl_2$ and $CrCl_2$) were obtained from Strem Chemicals Inc. and used as received. $NiCl_2 \cdot CH_3CN$ was prepared according to a literature procedure.[1] Potassium hydride (30 wt % dispersion in mineral oil; washed with hexane before use), was purchased from Sigma-Aldrich. 3-Methylbutanal, and tert-butyl amine were purchased from across organics. $SeO_2$ and pinacolone were purchased from Alfa Aesar.

$^1H$ and $^{13}C\{^1H\}$ NMR spectra were obtained at 400 and 100 MHz, respectively, in benzene-$d_6$ or chloroform-d as indicated and were referenced to the residual proton and the $^{13}C$ resonances of the solvents. Infrared spectra were obtained using Nujol as the medium. Magnetic moments were determined in the solid state using a Johnson Mathey magnetic susceptibility apparatus, and by, $^1H$ NMR in benzene solution using Evans method.[2] Melting points were determined on a Thermo Scientific Mel-Temp 3.0 digital melting point apparatus and are uncorrected. TGA and DTA were carried out with a SDT-2960 TGA/DTA instruments.

Preparation of
1-(tert-butylimino)-3-methylbutan-2-one

Isopropyl glyoxal[3-methyl-2-oxobutanal] was prepared using 3-methylbutanal and $SeO_2$ according to a published procedure.[5] A 100 mL round-bottomed flask was charged with a magnetic stir bar, 3-methyl-2-oxobutanal (1.000 g, 9.99 mmol) and diethyl ether (15 mL). To this stirred solution at ambient temperature was slowly added tert-butyl amine (1.059 g, 9.99 mmol). This solution was stirred for 6 h. The resultant yellow solution was washed with water (10 ml) and the organic layer was dried over anhydrous $Na_2SO_4$. The volatile components were removed by vacuum and resultant yellow oil was vacuum distilled. A light yellow oil was obtained at 60° C./0.05 Torr (1.147 g, 74%): IR (Nujol, cm$^{-1}$) 1697 (s), 1638 (m), 1383 (s), 1365 (s), 1347 (s), 1213 (s), 1191 (s), 1149 (s), 1087 (s), 1027 (m), 949 (s), 902 (s), 644 (m); $^1H$ NMR (CDCl$_3$, 23° C., δ) 7.48 (s, 1H, CHN), 3.57 (sep, 1H, J=7.2), CH(CH$_3$)$_2$), 1.19 (s, 9H, C(CH$_3$)$_3$), 1.04 (d, 6H, (J=7.2), CH(CH$_3$)$_2$); $^{13}C\{^1H\}$ NMR(CDCl$_3$, 23° C., ppm) 206.33 (s, CO), 118.93 (s, CHN), 58.40 (s, C(CH$_3$)$_3$), 33.92 (s, CH(CH$_3$)$_2$), 28.96 (s, C(CH$_3$)$_3$), 18.25 (s, CH(CH$_3$)$_2$).

Preparation of Bis(1-(tert-butylimino)-3-methylbut-2-en-2-olate)chromium(II) (12)

A 100 mL Schlenk flask was charged with a magnetic stir bar, 1-(tert-butylimino)-3-methylbutan-2-one (1.000 g, 6.44 mmol) and tetrahydrofuran (30 mL). To this stirred solution at ambient temperature was slowly added potassium hydride (0.284 g, 7.08 mmol), and solution was stirred for 4 hours. This solution was then slowly added dropwise by cannula to a stirred suspension of anhydrous chromium(II) chloride (0.393 g, 3.22 mmol) in tetrahydrofuran (40 mL) at −78° C. The resultant dark green solution was stirred for 15 hours at ambient temperature. The volatile components were then removed under reduced pressure, and the resultant dark green powder was dissolved in hexane (50 mL). The solution was filtered through a 1 cm pad of Celite on a coarse glass frit, and hexane was then removed under reduced pressure. Dark green crystals of 12 (0.115 g, 10%) were obtained by sublimation at 120° C./0.05 Torr: mp 150-152° C.; IR (Nujol, cm$^{-1}$) 1601 (m), 1580 (w), 1360 (m), 1352 (m), 1305 (m), 1215 (m), 971 (w); $\mu_{eff}$=4.80 and 4.98 $\mu_B$ in the solid state and in benzene solution, respectively Anal. Calcd for $C_{18}H_{32}CrN_2O_2$: C, 59.98; H, 8.95; N, 7.77. Found: C, 59.81; H, 8.86; N, 7.66.

Preparation of Bis(1-(tert-butylimino)-3-methylbut-2-en-2-olate)manganese(II) (13)

In a fashion similar to the preparation of 12, treatment of anhydrous manganese(II) chloride (0.403 g, 3.22 mmol) in tetrahydrofuran (40 mL) with a solution of potassium 1-(tert-butylimino)-3-methylbutan-2-olate (prepared from 1-(tert-butylimino)-3-methylbutan-2-one (1.000 g, 6.44 mmol) and KH (0.284 g, 7.08 mmol) in tetrahydrofuran (30 mL)) for 15 h at ambient temperature afforded 13 (0.429 g, 37%) as orange crystals upon sublimation at 165° C./0.05 Torr: mp 193-195° C.; IR (Nujol, cm$^{-1}$) 1609 (m), 1594 (m), 1365 (m), 1349 (m), 1310 (m), 1291 (m), 1218 (m), 1202 (m), 1031 (w), 956 (m), 798 (w); $\mu_{eff}$=8.45 and 7.89$\mu_B$ in the solid state and in benzene solution, respectively Anal. Calcd for $C_{18}H_{32}MnN_2O_2$: C, 59.49; H, 8.88; N, 7.71. Found: C, 59.39; H, 8.78; N, 7.64.

Preparation of Bis(1-(tert-butylimino)-3-methylbut-2-en-2-olate)iron(II) (14)

In a fashion similar to the preparation of 12, treatment of anhydrous iron(II) chloride (0.414 g, 3.22 mmol) in tetrahydrofuran (40 mL) with a solution of potassium 1-(tert-butylimino)-3-methylbutan-2-olate (prepared from 1-(tert-butylimino)-3-methylbutan-2-one (1.000 g, 6.44 mmol) and KH (0.284 g, 7.08 mmol) in tetrahydrofuran (30 mL)) for 15 h at ambient temperature afforded 14 (0.562 g, 49%) as dark red crystals upon sublimation at 155° C./0.05 Torr: mp 160-162° C.; IR (Nujol, cm$^{-1}$) 1600 (w), 1595 (w), 1350 (w), 1358 (m), 1300 (m), 1260 (m), 1090 (m), 1020 (m), 799 (m); $\mu_{eff}$=7.21 and 6.72$\mu_B$ in the solid state and in benzene solution, respectively Anal. Calcd for $C_{18}H_{32}FeN_2O_2$: C, 59.34; H, 8.85; N, 7.69. Found: C, 59.34; H, 8.76; N, 7.79.

Preparation of Bis(1-(tert-butylimino)-3-methylbut-2-en-2-olate)cobalt(II) (15)

In a fashion similar to the preparation of 12, treatment of anhydrous cobalt(II) chloride (0.418 g, 3.22 mmol) in tetrahydrofuran (40 mL) with a solution of potassium 1-(tert-butylimino)-3-methylbutan-2-olate (prepared from 1-(tert-butylimino)-3-methylbutan-2-one (1.000 g, 6.44 mmol) and KH (0.284 g, 7.08 mmol) in tetrahydrofuran (30 mL)) for 15 h at ambient temperature afforded 15 (0.933 g, 80%) as dark red crystals upon sublimation at 135° C./0.05 Torr: mp 166-168° C.; IR (Nujol, cm$^{-1}$) 1605 (m), 1588 (m), 1365 (m), 1348 (m), 1307 (m), 1290 (m), 1203 (m), 964 (m), 799 (m); $\mu_{eff}$=6.83 and 7.01 $\mu_B$ in the solid state and in benzene solution, respectively Anal. Calcd for $C_{18}H_{32}CoN_2O_2$: C, 58.85; H, 8.79; N, 7.62. Found: C, 59.02; H, 8.81; N, 7.67.

Preparation of Bis(1-(tert-butylimino)-3-methylbut-2-en-2-olate)nickel(II) (16)

In a fashion similar to the preparation of 12, treatment of anhydrous NiCl$_2$.CH$_3$CN (0.540 g, 3.22 mmol) in tetrahydrofuran (40 mL) with a solution of potassium 1-(tert-butylimino)-3-methylbutan-2-olate (prepared from 1-(tert-butylimino)-3-methylbutan-2-one (1.000 g, 6.44 mmol) and KH (0.284 g, 7.08 mmol) in tetrahydrofuran (30 mL)) for 15 h at ambient temperature afforded 16 (0.767 g, 66%) as pale green crystals upon sublimation at 120° C./0.05 Torr: mp 166-168° C.; IR (Nujol, cm$^{-1}$) 1607 (w), 1574 (m), 1358 (m), 1351 (m), 1299 (m), 1213 (m), 978 (w), 799 (w); $^1$H NMR (C$_6$D$_6$, 23° C., δ) 7.94 (s, 1H, CHN), 2.48 (s, 6H, C(CH$_3$)$_2$), 2.31 (s, 6H, C(CH$_3$)$_2$), 1.35 (s, 18H, C(CH$_3$)$_3$); $^{13}$C{$^1$H} NMR(C$_6$D$_6$, 23° C., ppm) 156.31 (s, CN), 150.64 (s, C(CH$_3$)$_2$), 126.95 (s, CO), 61.42 (s, C(CH$_3$)$_3$), 30.29 (s, C(CH$_3$)$_2$), 18.05 (s, C(CH$_3$)$_3$), 17.61 (s, C(CH$_3$)$_2$); Anal. Calcd for C$_{18}$H$_{32}$NiN$_2$O$_2$: C, 58.88; H, 8.78; N, 7.63. Found: C, 58.97; H, 8.89; N, 7.61.

Preparation of Bis(1-(tert-butylimino)-3-methylbut-2-en-2-olate)copper(II) (17)

In a fashion similar to the preparation of 12, treatment of anhydrous copper(II) chloride (0.430 g, 3.22 mmol) in tetrahydrofuran (40 mL) with a solution of potassium 1-(tert-butylimino)-3-methylbutan-2-olate (prepared from 1-(tert-butylimino)-3-methylbutan-2-one (1.000 g, 6.44 mmol) and potassium hydride (0.284 g, 7.08 mmol) in tetrahydrofuran (30 mL)) for 15 hours at ambient temperature afforded 17 (0.505 g, 43%) as brown crystals upon sublimation at 110° C./0.05 Torr: mp 135-138° C.; IR (Nujol, cm$^{-1}$) 1607 (m), 1586 (s), 1365 (m), 1350 (m), 1300 (s), 1239 (m), 1214 (s), 1126 (m), 1035 (m), 971 (m), 675 (m); $\mu_{eff}$=1.88 and 1.80$\mu_{13}$ in the solid state and in benzene solution, respectively Anal. Calcd for C$_{18}$H$_{32}$CuN$_2$O$_2$: C, 58.12; H, 8.67; N, 7.53. Found: C, 58.33; H, 8.76; N, 7.58.

Preparation of Bis(1-(test-butylimino)-3,3-dimethylbutan-2-oyl)chromium(II) (18)

In a fashion similar to the preparation of 12, treatment of anhydrous chromium(II) chloride (0.362 g, 2.95 mmol) in tetrahydrofuran (40 mL) with a solution of the lithium radical anion of 1-(tert-butylimino)-3,3-dimethylbutan-2-oyl (prepared from 1-(tert-butylimino)-3,3-dimethylbutan-2-one (1.000 g, 5.91 mmol) and lithium metal (0.045 g, 6.49 mmol) in tetrahydrofuran (30 mL)) for 15 h at ambient temperature afforded 18 (0.056 g, 5%) as brown crystals upon sublimation at 135° C./0.05 Torr: mp 248-250° C.; IR (Nujol, cm$^{-1}$) 1623 (w), 1489 (m), 1413 (w), 1367 (m), 1358 (m), 1341 (m), 1262 (w), 1200 (m), 1164 (m), 1062 (w), 984 (w).

Preparation of Bis(1-(tert-butylimino)-3,3-dimethylbutan-2-oyl)manganese(II) (19)

In a fashion similar to the preparation of 12, treatment of anhydrous manganese(II) chloride (0.365 g, 2.95 mmol) in tetrahydrofuran (40 mL) with a solution of the lithium radical anion of 1-(tert-butylimino)-3,3-dimethylbutan-2-oyl (prepared from 1-(tert-butylimino)-3,3-dimethylbutan-2-one (1.000 g, 5.91 mmol) and lithium metal (0.045 g, 6.49 mmol) in tetrahydrofuran (30 mL)) for 15 h at ambient temperature afforded 19 (0.407 g, 37%) as dark orange crystals upon sublimation at 145° C./0.05 Torr: mp 175-177° C.; IR (Nujol, cm$^{-1}$) 1650 (w), 1360 (m), 1344 (m), 1262 (w), 1211 (w), 1153 (w); $\mu_{eff}$=5.96 and 5.86 $\mu_B$ in the solid state and in benzene solution, respectively Anal. Calcd for C$_{40}$H$_{78}$Mn$_2$N$_4$O$_4$: C, 60.89; H, 9.97; N, 7.10. Found: C, 60.92; H, 10.04; N, 6.84.

Preparation of Bis(1-(tert-butylimino)-3,3-dimethylbutan-2-oyl)iron(II) (20)

In a fashion similar to the preparation of 12, treatment of anhydrous iron(II) chloride (0.381 g, 2.95 mmol) in tetrahydrofuran (40 mL) with a solution of the lithium radical anion of 1-(tert-butylimino)-3,3-dimethylbutan-2-oyl (prepared from 1-(tert-butylimino)-3,3-dimethylbutan-2-one (1.000 g, 5.91 mmol) and lithium metal (0.045 g, 6.49 mmol) in tetrahydrofuran (30 mL)) for 15 h at ambient temperature afforded 20 (0.210 g, 18%) as dark green crystals upon sublimation at 140° C./0.05 Torr: mp 143-145° C.; IR (Nujol, cm$^{-1}$) 1650 (m), 1365 (m), 1263 (w), 1214 (m), 1156 (w), 1125 (w), 1022 (w), 800 (w); $\mu_{eff}$=4.82 and 4.74 $\mu_B$ in the solid state and in benzene solution, respectively Anal. Calcd for C$_{40}$H$_{77}$Fe$_2$N$_4$O$_4$: C, 60.83; H, 9.83; N, 7.09. Found: C, 60.74; H, 9.60; N, 7.22.

Preparation of Bis(1-(tert-butylimino)-3,3-dimethylbutan-2-oyl)cobalt(II) (21)

In a fashion similar to the preparation of 12, treatment of anhydrous cobalt(II) chloride (0.383 g, 2.95 mmol) in tetrahydrofuran (40 mL) with a solution of the lithium radical anion of 1-(tert-butylimino)-3,3-dimethylbutan-2-oyl (prepared from 1-(tert-butylimino)-3,3-dimethylbutan-2-one (1.000 g, 5.91 mmol) and lithium metal (0.045 g, 6.49 mmol) in tetrahydrofuran (30 mL)) for 15 h at ambient temperature afforded 21 (0.869 g, 79%) as dark red crystals upon sublimation at 135° C./0.05 Torr: mp 194-196° C.; IR (Nujol, cm$^{-1}$) 1626 (w), 1482 (m), 1407 (m), 1332 (m), 1265 (w), 1216 (m), 1156 (m), 992 (w), 815 (w); $\mu_{eff}$=1.79 and 1.73 $\mu_B$ in the solid state and in benzene solution, respectively Anal. Calcd for C$_{20}$H$_{38}$CoN$_2$O$_2$: C, 60.44; H, 9.64; N, 7.05. Found: C, 60.42; H, 9.48; N, 7.07.

Preparation of Bis(1-(tert-butylimino)-3-methylbut-2-en-2-olate)nickel (II) (22)

In a fashion similar to the preparation of 12, treatment of anhydrous NiCl$_2$.CH$_3$CN (0.498 g, 2.95 mmol) in tetrahydrofuran (40 mL) with a solution of the lithium radical anion of 1-(tert-butylimino)-3,3-dimethylbutan-2-oyl (prepared from 1-(tert-butylimino)-3,3-dimethylbutan-2-one (1.000 g, 5.91 mmol) and lithium metal (0.045 g, 6.49 mmol) in tetrahydrofuran (30 mL)) for 15 h at ambient temperature afforded 22 (0.340 g, 30%) as red crystals upon sublimation at 135° C./0.05 Torr: mp 181-183° C.; IR (Nujol, cm$^{-1}$) 1633 (w), 1484 (m), 1407 (m), 1358 (s), 1264 (m), 1218 (m), 1158 (m), 991 (m), 887 (m), 818 (m), 761 (m), 621 (m); $^1$H NMR ($C_6D_6$, 23° C., δ) 9.93 (s, 1H, CHN), 2.27 (s, 9H, $C(CH_3)_3$), 0.70 (s, 9H, $C(CH_3)_3$); $^{13}C\{^1H\}$ NMR($C_6D_6$, 23° C., ppm) 148.50 (s, CO), 132.07 (s, CN), 73.63 (s, $C(CH_3)_3$), 54.56 (s, $C(CH_3)_3$), 23.26 (s, $C(CH_3)_2$), 15.30 (s, $C(CH_3)_3$); Anal. Calcd for $C_{20}H_{38}NiN_2O_2$: C, 60.47; H, 9.64; N, 7.05. Found: C, 59.95; H, 9.38; N, 7.06.

The following reaction scheme shows the synthesis of bis(1-(tert-butylimino)-3-methylbutan-2-olate) transition metal complexes.

The following reaction scheme shows the synthesis of bis(1-(tert-butylimino)-3,3-dimethylbutan-2-oyl) transition metal complexes.

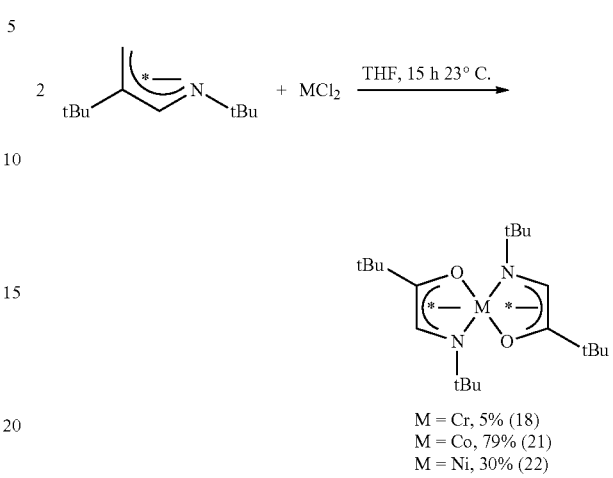

M = Cr, 5% (18)
M = Co, 79% (21)
M = Ni, 30% (22)

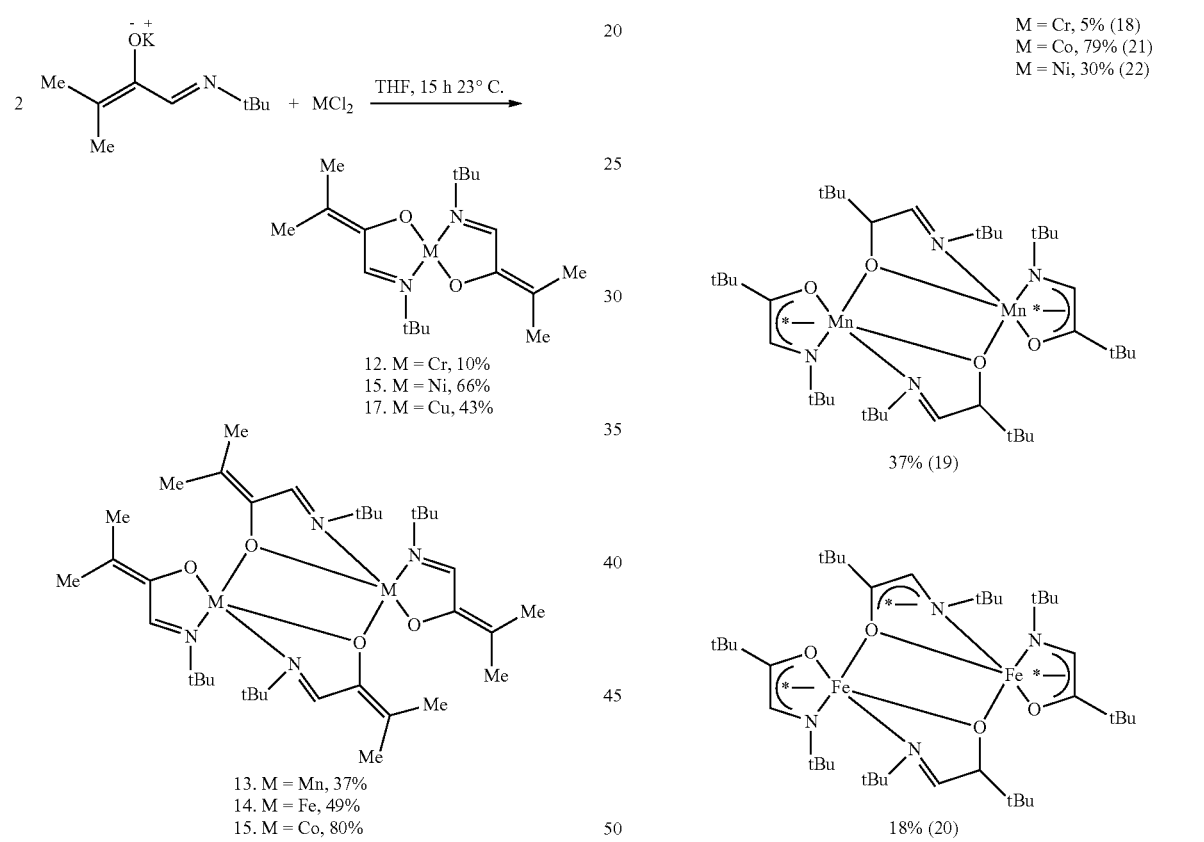

12. M = Cr, 10%
15. M = Ni, 66%
17. M = Cu, 43%

13. M = Mn, 37%
14. M = Fe, 49%
15. M = Co, 80%

37% (19)

18% (20)

TABLE 2

Thermal properties of 12-17.

| Compound | Isolated yield by sublimation (%) | Sublimation temperature (° C./0.05 Torr) | Melting point (° C.) | Solid state decomposition temperature (° C.) | % Recovery | % Non volatile residue |
|---|---|---|---|---|---|---|
| 12 | 10 | 120 | 150-152 | 220 | 96 | 3 |
| 13 | 37 | 165 | 193-195 | 295 | 97 | 2 |
| 14 | 49 | 155 | 160-162 | 262 | 97 | 2 |
| 15 | 80 | 135 | 166-168 | 276 | 98 | <1 |
| 16 | 66 | 120 | 166-168 | 260 | 97 | 2 |
| 17 | 43 | 110 | 135-138 | 190 | 97 | 2 |

TABLE 3

Thermal properties of 18-22.

| Compound | Isolated yield by sublimation (%) | Sublimation temperature (° C./0.05 Torr) | Melting point (° C.) | Solid state decomposition temperature (° C.) | % Recovery | % Non-volatile residues |
|---|---|---|---|---|---|---|
| 18 | 5  | 135 | 248-250 | 250 | 90 | 7 |
| 19 | 37 | 145 | 175-177 | 245 | 91 | 6 |
| 20 | 18 | 140 | 143-145 | 241 | 90 | 8 |
| 21 | 79 | 135 | 194-196 | 235 | 93 | 6 |
| 22 | 30 | 135 | 181-183 | 180 | 90 | 5 |

Figure 6:
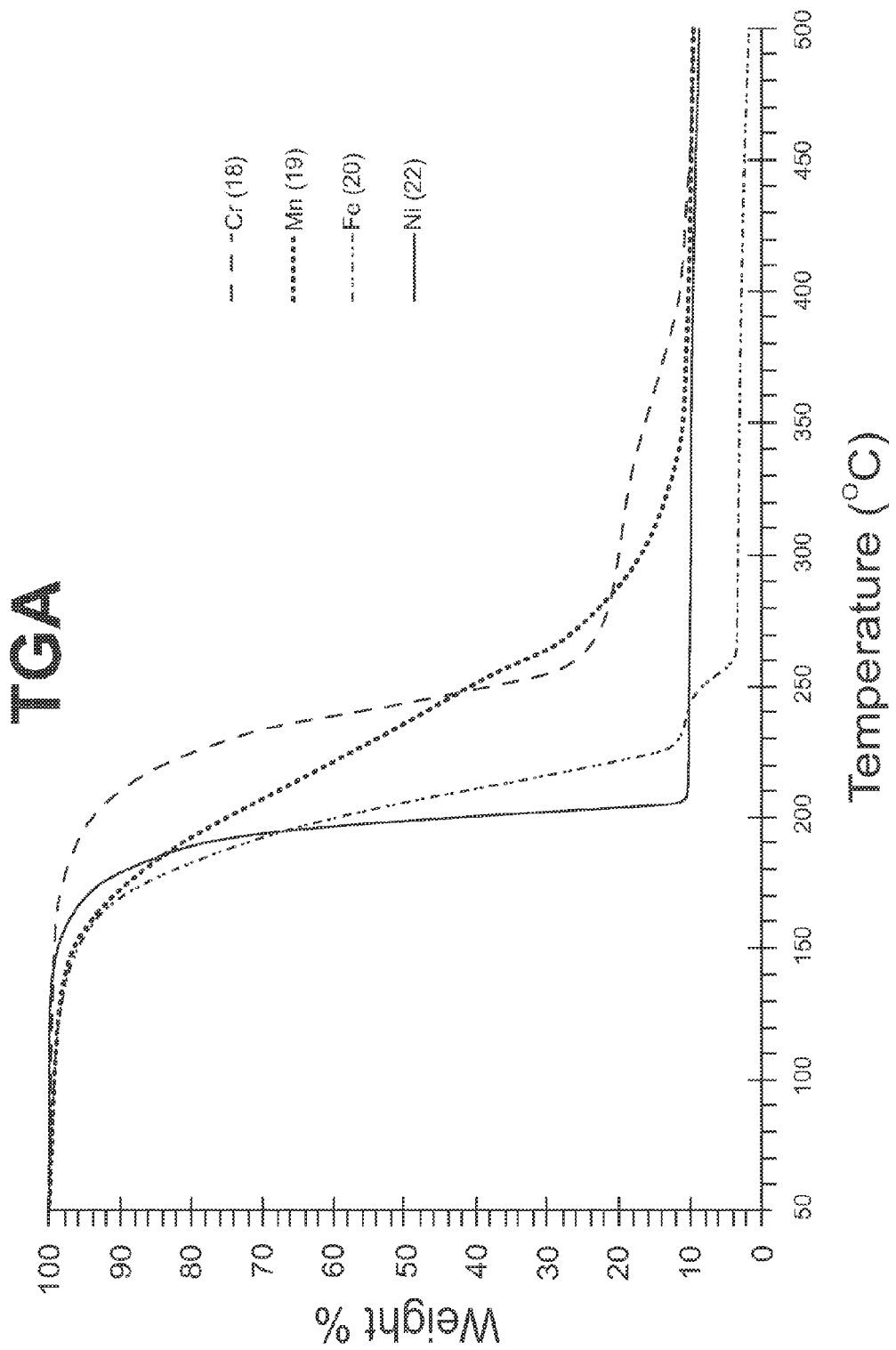
FIG. 6 provides thermogravimetric analysis (TGA) for compounds 18-20, and 22.

FIG. 6 provides TGA traces of compounds 18-20, and 22.

Solution Phase Reactivity.

Figure 7:
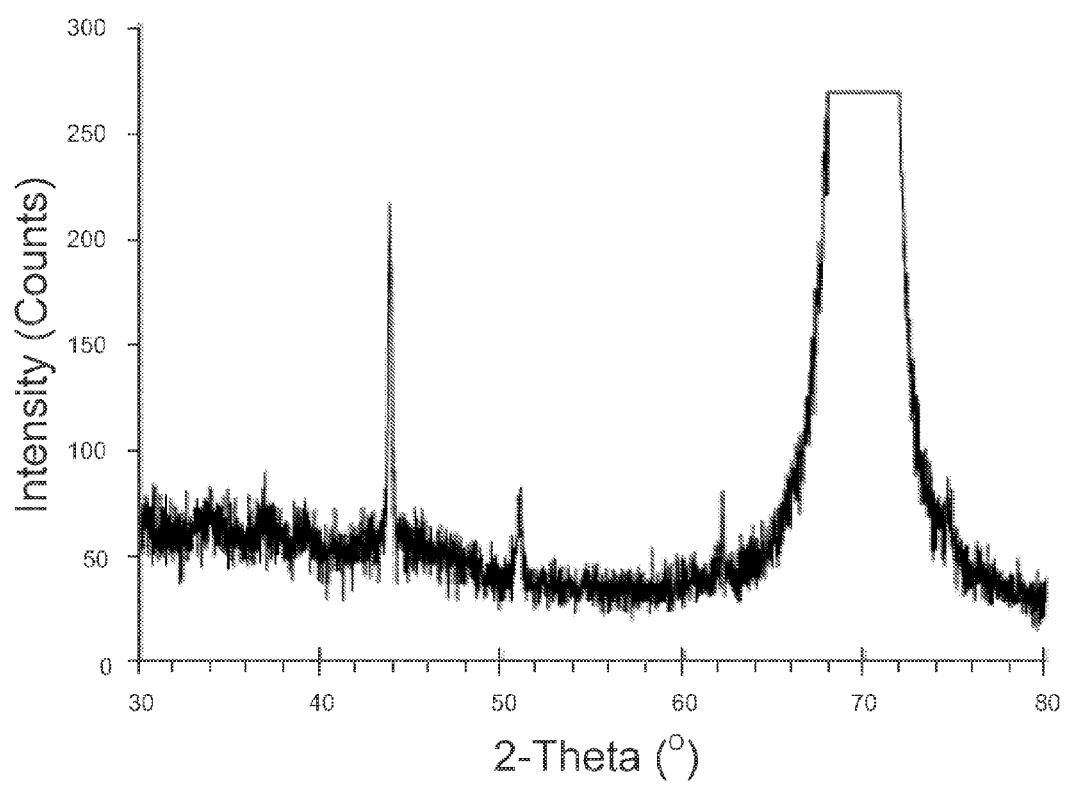
FIG. 7 provides an X-ray powder diffraction spectrum of copper metal produced upon treatment of 17 with $BH_3$ ($NHMe_2$)
Figure 8:
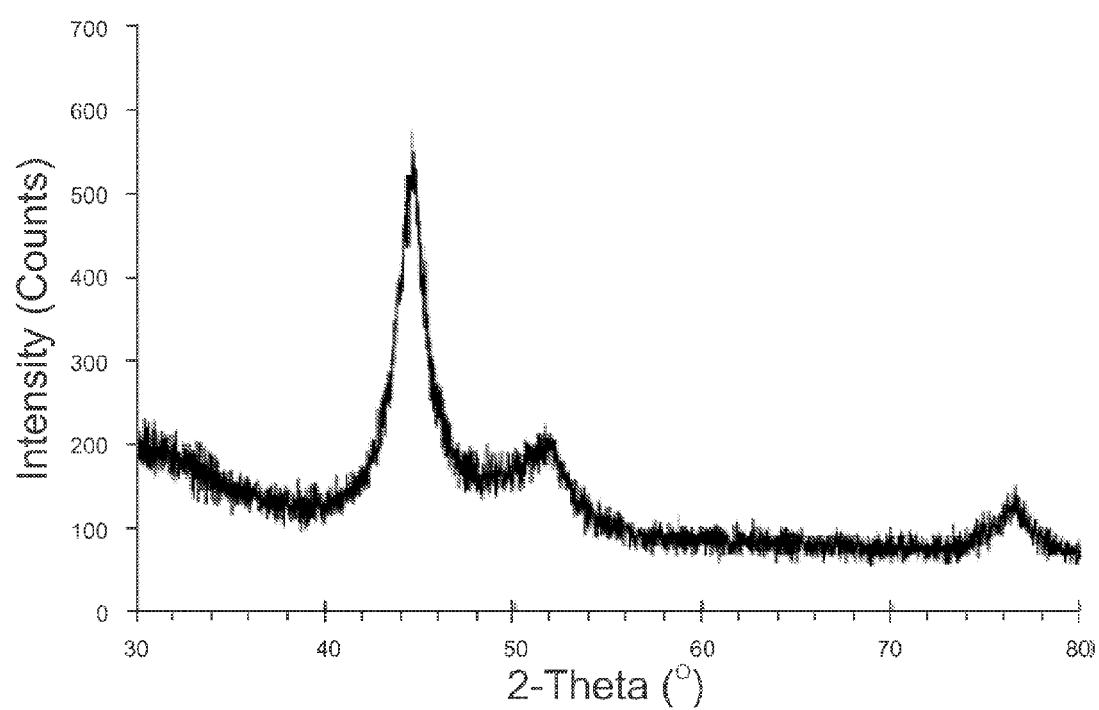
FIG. 8 provides an X-ray powder diffraction spectrum of nickel metal produced upon treatment of 16 with $BH_3$ ($NHMe_2$).

In order to get some insight into reactivity of these precursors, 15-17 were treated with reducing co-reagents. In these reactions, a solution of 15-17 in tetrahydrofuran was treated with 5-times molar excess of $NH_2NH_2$ and $BH_3$ ($NHMe_2$) in separate flasks. Reactions that did not afford a black powder or black solution at ambient temperature within one hour were then refluxed for one hour. Results are summarized in Table 4. Treatment of 17 with $NH_2NH_2$ and $BH_3(NHMe_2)$ afforded a copper colored powder which gave reflections for copper metal in X-ray powder diffraction (FIG. 7). Additionally, 16 reacted with both reducing agents at ambient temperature to afford nickel metal which was confirmed by X-ray powder diffraction (FIG. 8). Moreover, 15 reacted with $BH_3(NHMe_2)$ at ambient temperature and gave a black precipitate which stuck to stir bar, suggesting the formation of cobalt metal. However, X-ray powder diffraction did not show reflections. Treatment of 15 with $NH_2NH_2$ did not afford a black solution or black precipitate either at ambient temperature or reflux condition.

TABLE 4

Reactivity of 15-17 toward reducing agents in tetrahydrofuran.

| Reducing agent | $(CoL_2)_2$ (15) | $NiL_2$ (16) | $CuL_2$ (17) |
|---|---|---|---|
| $NH_2NH_2$ | No change | metallic mirror on the flask wall | copper colored powder |
| $BH_3(NHMe_2)$ | Black powder; sticks to stir bar | black powder; sticks to stir bar | copper colored powder |

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

REFERENCES

Reedijk, J.; Groeneveld, W. L. *Rect. Tray. Chim. Pays-Bas* 1968, 87, 552.

Evans, D. F. *J. Chem. Soc.* 1959, 2003.

McNab, H. *J. Chem. Soc., Perkin Trans.* 2 1981, 1283.

Severin, T.; Poehlmann, H. *Chem. Ber.* 1977, 110, 491.

Kwiatowski, P.; Chaladaj, W.; Jurczak, J. *Tetrahedron* 2006, 62, 5116-5125.

What is claimed is:

1. A compound having formula (I):

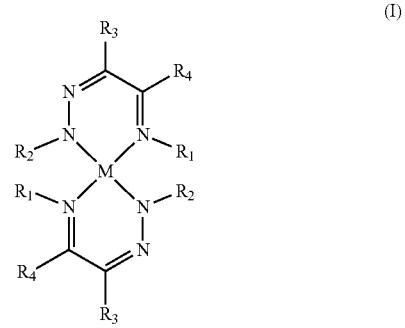

(I)

wherein:
M is a metal selected from groups 2 to 12 of the Periodic Table;
$R_1$ is $C_{1-8}$ alkyl, $C_{5-12}$ aryl, or $NR_5R_6$;
$R_2$ is $C_{1-8}$ alkyl;
$R_3$, $R_4$ are each independently hydrogen or $C_{1-8}$ alkyl; and
$R_5$, $R_6$ are each independently $C_{1-8}$ alkyl with the proviso that when M is Cr, $R_5$ is $C_{2-8}$ alkyl.

2. The compound of claim 1 wherein M is Zn, Mg, Cr, Mn, Fe, Co, Ni, or Cu.

3. The compound of claim 1 wherein $R_2$ is t-butyl.

4. The compound of claim 1 wherein when $R_1$ is $C_{1-8}$ alkyl, M is Zn, Mg, Cr, Mn, Fe, Co, or Ni, and when $R_1$ is $NR_5R_6$, M is Zn, Mg, Mn, Fe, Co, or Ni.

5. The compound of claim 1 wherein $R_1$ is $C_{1-8}$ alkyl and M is Zn, Mg, Cr, Mn, Fe, Co, or Ni.

6. The compound of claim 1 wherein $R_1$ is $NR_5R_6$ and M is Zn, Mg, Mn, Fe, Co, or Ni.

7. The compound of claim 1 wherein $R_1$ is $C_{1-8}$ alkyl.

8. The compound of claim 1 wherein $R_1$ is methyl, ethyl, n-propyl, isopropyl, n-butyl, sec-butyl, isobutyl, t-butyl, or phenyl.

9. The compound of claim 1 wherein $R_1$ is t-butyl or $N(CH_3)_2$.

10. A compound having formula 2:

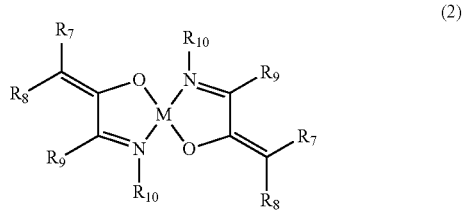

(2)

wherein:
M is a metal selected from groups 2 to 12 of the Periodic Table;
$R_7$, $R_8$, $R_9$ are each independently hydrogen, $C_{1-8}$ alkyl, $C_{5-12}$ aryl, or $C_{5-12}$ heteroaryl; and
$R_{10}$ is $C_{1-8}$ alkyl, $C_{5-12}$ aryl, or $C_{5-12}$ heteroaryl.

11. The compound of claim 10 wherein M is Zn, Mg, Cr, Mn, Fe, Co, Ni, or Cu.

12. The compound of claim 10 wherein $R_7$, $R_8$, $R_9$, $R_{10}$ are each independently $C_{1-8}$ alkyl.

13. The compound of claim 10 wherein $R_{10}$ is t-butyl.

14. A compound having formula (3):

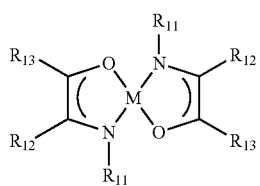

(3)

M is a metal selected from groups 2 to 12 of the Periodic Table;
$R_{11}$ is $C_{1-8}$ alkyl, $C_{5-12}$ aryl, or $C_{5-12}$ heteroaryl; and
$R_{12}$, $R_{13}$ are each independently hydrogen, $C_{1-8}$ alkyl, $C_{5-12}$ aryl, or $C_{5-12}$ heteroaryl.

15. The compound of claim 14 wherein M is Zn, Mg, Cr, Mn, Fe, Co, Ni, or Cu.

16. A method comprising:
a) reacting a compound having bidentate ligands with an reactive compound to form a first product, the compound having bidentate ligands being selected from the group consisting of:

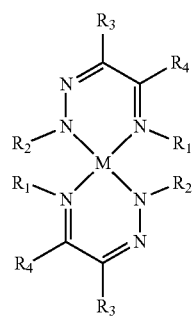

(1)

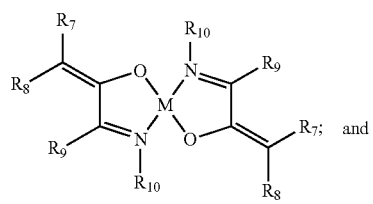

(2)

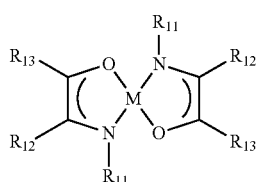

(3)

wherein:
M is a metal selected from groups 2 to 12 of the Periodic Table;
$R_1$ is $C_{1-8}$ alkyl, $C_{5-12}$ aryl, or $NR_5R_6$;
$R_2$ is $C_{1-8}$ alkyl;
$R_3$, $R_4$ are each independently hydrogen or $C_{1-8}$ alkyl;
$R_5$, $R_6$ are each independently $C_{1-8}$ alkyl with the proviso that when M is Zn, Mg, Cr, $R_5$ is $C_{2-8}$ alkyl;
$R_7$, $R_8$, $R_9$ are each independently hydrogen, $C_{1-8}$ alkyl, $C_{5-12}$ aryl, or $C_{5-12}$ heteroaryl; and
$R_{10}$ is $C_{1-8}$ alkyl, $C_{5-12}$ aryl, or $C_{5-12}$ heteroaryl;
$R_{11}$ is $C_{1-8}$ alkyl, $C_{5-12}$ aryl, or $C_{5-12}$ heteroaryl; and
$R_{12}$, $R_{13}$ are each independently hydrogen, $C_{1-8}$ alkyl, $C_{5-12}$ aryl, or $C_{5-12}$ heteroaryl.

17. The method of claim 16 wherein M is Zn, Mg, Cr, Mn, Fe, Co, or Ni.

18. The method of claim 16 wherein the reactive compound is an oxidizing agent and the first product includes a metal oxide.

19. The method of claim 16 wherein the reactive compound is a reducing agent and the first product includes a metal in the zero oxidation state.

20. The method of claim 16 wherein the activating reactive compound is a nitriding agent and the first product includes a metal nitride.

21. The method of claim 16 comprising a deposition cycle including:
a) contacting a substrate with a vapor of the compound having bidentate ligands form a first modified surface; and
c) contacting the substrate with the reactive compound.

22. The method of claim 21 wherein a metal-containing layer is deposited on the substrate.

23. The method of claim 22 wherein the metal-containing layer includes a component selected from the group consisting of metals in the zero oxidation state, metal nitrides, metal oxides, and combinations thereof.

24. The method of claim 21 further comprising contacting the first modified surface with an acid.

25. The method of claim 16 wherein the compound having bidentate ligands has formula 1:

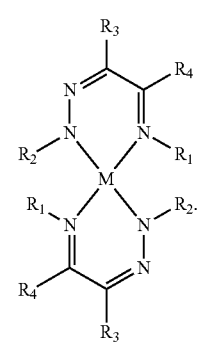

(1)

26. The method of claim 25 wherein M is Zn, Mg, Cr, Mn, Fe, Co, or Ni.

* * * * *